(12) United States Patent
Allen et al.

(10) Patent No.: US 6,849,783 B2
(45) Date of Patent: Feb. 1, 2005

(54) PLANT BIOTIN SYNTHASE

(75) Inventors: Stephen M. Allen, Wilmington, DE (US); Emil M. Orozco, Jr., Cochranville, PA (US); Anthony J. Kinney, Wilmington, DE (US); Guo-Hua Miao, Johnston, IA (US)

(73) Assignee: E. I. Dupont de Nemours & Company, Wilmington, DE (US)

( * ) Notice: Subject to any disclaimer, the term of this patent is extended or adjusted under 35 U.S.C. 154(b) by 186 days.

(21) Appl. No.: 09/740,288

(22) Filed: Dec. 19, 2000

(65) Prior Publication Data

US 2001/0039042 A1 Nov. 8, 2001

Related U.S. Application Data

(60) Provisional application No. 60/172,929, filed on Dec. 21, 1999.
(51) Int. Cl.⁷ .......................... A01H 11/00; C12P 17/18; C12N 9/00; C12N 15/00; C07H 21/04
(52) U.S. Cl. ...................... 800/295; 435/419; 435/183; 435/320.1; 536/232
(58) Field of Search ............................... 435/183, 25.3, 435/91.1, 252.3, 254.2, 419, 69.1, 468, 320.1; 536/23.2; 800/295, 300.1

(56) References Cited

U.S. PATENT DOCUMENTS

| 5,859,335 A | 1/1999 | Patton | 800/205 |
| 5,869,719 A | 2/1999 | Patton | 800/278 |

OTHER PUBLICATIONS

Max A. Eisenberg, Adv. Enzymology, vol. 38:317–372, 1973, Biotin: Biogenesis, Transport, and their Regulation.
C.H. Pai, Journ. of Bacteriology, vol. 121(1):1–8, 1/1975, Genetics of Biotin Biosynthesis in *Bacillus subtilis*.
Jeremy R. Knowles, Ann. Rev. Biochem., vol. 58:195–221, 1989, The Mechanism of Biotin–Dependent Enzymes.
Olwen M. Birch et al., J. Biol. Chem., vol. 270:19158–19165, 1995, Biotin Synthase form *Escherichia coli*, an Investigation of the Low Molecular Weight and Protein Components Required for Activity in Vitro.

Pierre Baldet et al., Eur. J. Biochem., vol. 217:479–485, 1993, Biotin Biosynthesis in higher plant cells.
David A. Patton et al., Plant Physiol., vol. 116:935–946, 1998, An Embryo–Defective Mutant of Arabidopsis Disrupted in the Final Step of Biotin Synthesis.
National Center for Biotechnology Information General Identifier No. 1705463, Oct. 1, 2000, Weaver, L.M. et al., Characterization of the cDNA and gene coding for the biotin synthase of *Arabidopsis thaliana*.
Lisa M. Weaver et al., Plant Physiol., vol. 110:1021–1028, 1996, Characterization of the cDNA and gene coding for the biotin synthase of *Arabidopsis thaliana*.
Pierre Baldet et al., C.R. Acad. Sci., vol. 319:99–106, 1996, Biotin Synthesis in higher plants: isolation of a cDNA encoding *Arabidopsis* thaliana bioB–gene product Equiivalent by functional complementation of a biotin auxotroph mutant bioB105 of *Escherichia coli* K12.
Xiaoying Lin et al., Nature, vol. 402:761–768, Dec. 16, 1999, Sequence and analysis of chromosome 2 of the plant *Arabidopsis thaliana*.
National Center for Biotechnology Information General Identifier No. 2995363, Apr. 6, 1999, Wood, V. et al.,
National Center for Biotechnology Information General Identifier No. 6321725, Jan. 30, 2001, Goffeau, A. et al., Life with 6000 genes.
A. Goffeau et al., Science, vol. 274:546–567, Oct. 25, 1996, Life with 6000 Genes.
H. Tettelin et al., Nature, vol. 387(6632 suppl):81–84, 1997, The nucleotide sequence of *Saccharomyces cerevisiae* chromosome VII.

*Primary Examiner*—Ponnathapu Achutamurthy
*Assistant Examiner*—Malgorzata A Walicka
(74) *Attorney, Agent, or Firm*—Connolly Bove Lodge & Hutz LLP

(57) ABSTRACT

This invention relates to an isolated nucleic acid fragment encoding a biotin synthases. The invention also relates to the construction of a chimeric gene encoding all or a portion of the biotin synthases, in sense or antisense orientation, wherein expression of the chimeric gene results in production of altered levels of the biotin synthases in a transformed host cell.

13 Claims, 3 Drawing Sheets

Alignment of Biotin Synthase Proteins from Barley (SID18), Corn (SID 20-24), Prickly Poppy (SID 26), Soybean (SID 28), and Wheat (SID 32)

```
SID18     TTTPS-------AVSP--SAAAAPFRPALLAE---PAMMLLLARSLRSRVRSPFASAVSAAPFSSVSAAPFSSVSAAAAEAERAVRDGPRNDWTRP
SID20     MA---------------------------------LMLLARNLRSRLRPPLAA---AAAFSS----AAAEAERAIRDGPRNDWSRP
SID22     MA---------------------------------LMLLARNLRSRLRPPLAA---AAAFSS----AAAEAERAIRDGPRNDWSRP
SID24     MA---------------------------------LMLLARNLRSRLRPPLAA---AAAFSS----AAAEAERAIRDGPRNDWSRP
SID26     ----------------MLKVQSL-RAR--------LRPLIFIS-----TFSSLSSSSSAAAVQAERTIKEGPRNDWSRD
SID28     TKPNPKHKYRCCLLSLSCLYSQISHSFSVVSLPNFEFESKNMFLARPIFRA--PSLWALHSSYAYSSASAAAIQAERAIKEGPRNDWSRD
SID32     T------------------------------------------------------------------------------
1705463   -------MMLVRSVFRSQ-----------------LRPSV-SG-----GLQSASCYSSLSAASAEAERTIREGPRNDWSRD
SID30     MAT----LRTSLSRSLILLRSNTPKLAPIS-----SSVRLQVQKSRNYGTVSSVPPQATETSSTSPSKDVYQEALNATE-PRSNWTRE
2995363   M------------------------------FT---RTIRQQIRRSSALSLV-------------------RNNWTRE
6321725   M------MSTIYRHLSTA--RPALTKYATNAA--VKSTTASSEASTLGALQYALSL-----------------DEPSHSWTKS

SID18     EIQAIYDSPLLDLLFHGAQVHRNVHKFREVQQCTLLSIKTGGCSEDCSYCPQSSRYSTGLKAEKLMKKDAVLEAAKKAKEAGSTRFCMGA
SID20     EIQAVYDSPLLDLLFHGAQ-----------------------------SSRYNTGLKAQKLMNKYAVLEAAKKAKESGSTRFCMGA
SID22     EIQAVYDSPLLDLLFHGAQVHRNVHKFREVQQCTLLSIKTGGCSEDCSYCPQSSRYNTGLKAQKLMNKDAVLEAAKKAKESGSTRFCMGA
SID24     EIQAVYDSPLLDLLFHGAQVHRNVHKFREVQQCTLLSIKTGGCSEDCSYCPQSSRYNTGLKAQKLMNKYAVLEAAKKAKESGSTRFCMGA
SID26     EIKSVYDSPVLDLLFHAAQVHRHAHNFREVQQCTLLSVKTGGCSEDCSYCPQSSRYDTGVKAQKLMNKDAVLQAAEKAKEAGSTRFCMGA
SID28     QVKSIYDSPILDLLFHGAQVHRHAHNFREVQQCTLLSIKTGGCSEDCSYCPQSSKYDTGVKGQRLMNKEAVLQAAKKAKEAGSTRFCMGA
SID32     ---------------------------------------------------------RDAVLEAAKKAKEAGSTRFCMGA
1705463   EIKSVYDSPLLDLLFHGAQVHRHVHNFREVQQCTLLSIKTGGCSEDCSYCPQSSRYCPQSSRYSTGVKAQRLMSKDAVIDAAKKAKEAGSTRFCMGA
SID30     EIKAIYDKPLMELCWGAGSLHRKFHIPGAIQMCTLLNIKTGGCSEDCSYCAQSSRYQTGLKASKMVSVESVLAAARIAKDNGSTRFCMGA
2995363   EIQKIYDTPLIDLIFRAASIHRKFPHDPKKVQQCTLLSIKTGGCTEDCKYCAQSSRYNTGVKATKLMKIDEVLEKAKIAKAKGSTRFCMGS
6321725   QLKEIYHTPLLELTHAAQLQHRKWHDPTKVQLCTLMNIKSGGCSEDCKYCAQSSRNDTGLKAEKMVKVDEVIKEAEEAKRNGSTRFCLGA
```

FIG. 1A

```
SID18     AWRETIGRKTNFNQILEYVKDIRGMGMEVCCTLGMLEKQQAEELKKAGLTAYNHNLDTSREYYPNIISTRSYDDRLQTLQHVREAGISVC
SID20     AWRETIGRKSNFNQILEYVKEIRGMGMEVCCTLGMIEKQQAEELKKAGLTAYNHNLDTSREYYPNIITTRSYDDRLQTLEHVREAGISIC
SID22     AWRETIGRKSNFNQILEYVKEIRGMGMEVCCTLGMIEKQQAEELKKAGLTAYNHNLDTSREYYPNITTRSYDDRLQTLEHVREAGISIC
SID24     AWRETIGRKSNFNQILEYVKEIRGMGMEVCCTLGMIEKQQAEELKKAGLTAYNHNLDTSREYYPNIITTRSYDDRLQTLEHVREAGISIC
SID26     AWRDTVGRKTNFKQILEYVKEIRGMGMEVCCTLGMIEKQQAVELKQAGLTAYNHNLDTSREYYPNIITTRSYDERLETLQFVREAGINVC
SID28     AWRDTLGRKTNFNQILEYVKDIRDMGMEVCCTLGMLEKQQAVELKKAGLTAYNHNLDTSREYYPNITTRTYDERLQTLEFVRDAGINVC
SID32     AWRETIGRKTNFNQILEYVKDIRGMGMEVCCTLGMLEKQQAEELKKAGLTAYNHNLDTSREYYPNIISTRSYDDRLQTLQHVREAGISVC
1705463   AWRDTIGRKTNFSQILEYIKEIRGMEVCCTLGMIEKQQALELKKAGLTAYNHNLDTSREYYPNVITTRSYDDRLETLSHVRDAGINVC
SID30     AWRDMRGRKTNLKNVKTMVSEIRGMGMEVCVTLGMIDAEQAQELKEAGLTAYNHNVDTSRDFYPKVITTRTYDERLDTIKNVREAGINVC
2995363   AWRDLNGRNRTFKNILEIIKEVRSMDMEVCVTLGMLNEQQAKELKDAGLTAYNHNLDTSREYYSKIISTRTYDERLNTIDNLRKAGLKVC
6321725   AWRDMKGRKSAMKRIQEMVTKVNDMGLETCVTLGMVDQDQAKQLKDAGLTAYNHNIDTSREHYSKVITTRTYDDRLQTIKNVQESGIKAC

SID18     SGGIIGLGEAEEDRVGLLHTLATLPTHPESVPINALIAVKGTPLQD--QKP----VEIWEMIRMIASARIVMPKAMVRLSAGRVRFSMPE
SID20     SGGIIGLGEAEEDRVGLLHTLATLPTHPESVPINALVAVKGTPLED--QKP----VEIWEMIRMIATARITMPKAMVRLSAGRVRFSMPE
SID22     SGGIIGLGEAEEDRVGLLHTLATLPTHPESVPINALVAVKGTPLED--QKP----VEIWEMIRMIATARITMPKAMVRLSAGRVRFSMPE
SID24     SGGIIGLGEAEEDRVGLLHTLATLPTHPESVPINALVAVKGTPLED--QKP----VEIWEMIRMIATARIVMPKAMVRLSAGRVRFSMPE
SID26     SGGIIGLGEAEEDRVGLLHTLATLPSHPESVPINALLAVKGTPLED--QKP----VEIWEMIRMIATARIVMPKAMVRLSAGRVRFSMSE
SID28     SGGIIGLGEAEEDRVGLLHTLSTLPTHPESVPINALVAVKGTPLED--QKP----VEIWEMIRMIATARIVMPKAMVRLSAGRVRFSMPE
SID32     SGGIIGLGEAEEDRVGLLHTLATLPTHPESVPINALIAVKGTPLQD--QKP----VEIWEMIRMIASARIVMPKAMVRLSAGRVRFSMPE
1705463   SGGIIGLGEAEEDRIGLLHTLATLPSHPESVPINALLAVKGTPLEG--QKP----VEIWEMIRMIGTARIVMPKAMVRLSAGRVRFSMSE
SID30     TGGILGLGENKSDHIGLLETVATLPSHPESFPVNMLVAIKGTPLEG--NKK----VEFENMLRMVATARIVMPKTIVRLAAGRGELSEEQ
2995363   SGGILGLGEKKHDRVGLIHSLATMPTHPESVPFNLLVPIPGTPVGDAVKER---LPIHPFLRSIATARICMPKTIIRFAAGRNTCSESE
6321725   TGGILGLGESEDDHIGFIYTLSNMSPHPESLPINRLVAIKGTPMAEELADPKSKKLQFDEILRTIATARIVMPKAIIRLAAGRYTMKETE
```

FIG. 1B

```
SID18    QALCFLAGANSIFAGEKLLTTANNDFDADQAMFKILGLIPKAP------NFGDEEATVASSTE--RCEQ--AASM
SID20    QALCFLAGANSIFAGEKLLTTANNDFDADQAMFKILGLIPKAP-----SFGEEEASAAAPTESERSEQ--AASM
SID22    QALCFLAGANSIFAGEKLLTTANNDFDADQAMFKILGLIPKAP-----SFGEEEVSAAAPAESERSEQ--AASM
SID24    QALCFLAGANSIFAGEKLLTTANNDFDADQAMFKILGLIPKAP-----SFGEEEASAAAPTESERSEQ--AASM
SID26    QALCFLAGANSIFTGEKLLTTPNNDFDADQMMFKILGLTPKAP-------NFDQTS----TSFEAERCEQEATAS-
SID28    QALCFLAGANSIFTGEKLLTTPNNDFDADQLMFKVLGLLPKAP--------SLHEGE----TSVTEDY--KEAASSS
SID32    QALCFLAGANSIFAGEKLLTTANNDFDADQAMFKILGLIPKAP------NFGDEEVMVAAPTE--RCEQ--AALM
1705463  QALCFLAGANSIFTGEKLLTTPNNDFDADQLMFKTLGLIPKPP------S--ESENCEKVASASH
SID30    QVLCFMAGANAVFTGETMLTTPAVGWGVDSVVFNRWGLRPMESFEVEALKNDKPATTNTEIPVEASKAEMPGTVA
2995363  QALAFMAGANAVFTGEKMLTTPAVSWDSDSQLFYNWGLEGMQSFEYGT---STEGEDGTFTLPPKERLAPSPSL
6321725  QFVCFMAGCNSIFTGKKMLTTMCNGWDEDKAMLAKWGLQPMEAFKYD----------------RS
```

FIG. 1C

Clone cdt2c.pk002.c17 Contains a 99 Nucleotide Deletion

```
SID19 CGACTGGAGCCGGCCGGCCCGAGATCCAGGCCGTCTACGACTCACCGCTCCTCGACCTCCTCTT
SID21 CGACTGGAGCCGGCCGGCCCGAGATCCAGGCCGTCTACGACTCACCGCTCCTCGACCTCCTCTT

SID19 TCACGGGGCTCAG---------------------------------------------------
SID21 TCACGGGGCTCAGGTCCACAGAAATGTCCATAAATTCAGAGAAGTGCAGCAATGCACACT

SID19 ------------------------------------------------TCATCAAG
SID21 TCTTTCAATCAAGACTGGTGGATGCAGTGAAGATTGTTCTTACTGTCCTCAGTCATCAAG

SID19 ATACAACACTGGATTGAAGGCCCAAAAATTGATGAACAAATATGCTGTCTTGGAAGCAGC
SID21 ATACAACACTGGATTGAAGGCCCAAAAATTGATGAACAAAGATGCTGTCTTGGAAGCAGC
```

FIG. 2

PLANT BIOTIN SYNTHASE

This application claims the benefit of U.S. Provisional Application No. 60/172,929, filed Dec. 21, 1999.

FIELD OF THE INVENTION

This invention is in the field of plant molecular biology. More specifically, this invention pertains to nucleic acid fragments encoding biotin synthase in plants and seeds.

BACKGROUND OF THE INVENTION

Biotin is an essential component for all living organisms even though many, including humans, cannot synthesize biotin and are dependent upon its uptake from their environment or diet (Eisenberg (1973) *Adv Enzymol* 38:317–372, Pai (1975) *J Bacteriol* 121:1–8). Biotin serves as a cofactor that covalently binds to carboxylases and facilitates the transfer of carboxyl groups during enzymatic reactions involving carboxylation, decarboxylation and transcarboxylation (Dakshinamurti and Bhagavan, eds., (1985) "Biotin ", *Ann NY Acad Sci* 447:1–441; Knowles (1989) *Ann Rev Biochem* 58:195–221).

Biotin biosynthesis has been extensively studied in microorganisms, using biotin auxotrophic mutants to characterize the pathway. The biosynthesis of biotin involves four enzymatic steps in all microorganisms that starts with the precursor pimeloyl-CoA. The final step in this pathway involves the addition of sulfur to desthiobiotin to form biotin. The enzyme responsible for this reaction is known as biotin synthase and is encoded by the bioB gene (Birch et al. (1995) *J Biol Chem* 270:19158–19165).

The biotin biosynthetic pathway in plant cells has also been elucidated biochemically (Baldet (1993) *Eur J Biochem* 217:479–485) and genetically (Patton et al. (1998) *Plant Physiol* 116:935–946. This pathway is very similar to the bacterial pathways. Recent work has shown that increasing the level of biotin synthase activity in cells can direct the production of more biotin (U.S. Pat. No. 5,859,335 and 5,869,719). The present invention describes the identification of several new plant genes encoding biotin synthase. The use of these genes in plants as targets for herbicide treatment is disclosed.

SUMMARY OF THE INVENTION

The present invention concerns an isolated polynucleotide comprising a nucleotide sequence selected from the group consisting of: (a) a first nucleotide sequence encoding a polypeptide of at least 52 amino acids having at least 85% identity based on the Clustal method of alignment when compared to a second polypeptide selected from the group consisting of SEQ ID NOs:2, 4, 6, 8, 10, 12, 14, and 16, or preferably a third polypeptide of at least 100 amino acids, the polypeptide having a sequence identity of at least 85% identity based on the Clustal method of alignment when compared to a fourth polypeptide selected from the group consisting of SEQ ID NOs:18, 20, 22, 24, 26, 28, 30, and 32, and (b) a second nucleotide sequence comprising the complement of the first nucleotide sequence.

In a second embodiment, it is preferred that the isolated polynucleotide of the invention comprises a first nucleotide sequence which comprises a nucleic acid sequence selected from the group consisting of SEQ ID NOs:1, 3, 5, 7, 9, 11, 13, 15, 17, 19, 21, 23, 25, 27, 29, and 31, that codes for the polypeptide selected from the group consisting of SEQ ID NOs:2, 4, 6, 8, 10, 12, 14, 16, 18, 20, 22, 24, 26, 28, 30, and 32.

In a third embodiment, this invention concerns an isolated polynucleotide comprising a nucleotide sequence of at least 150 (preferably at least 400, most preferably at least 600) contiguous nucleotides derived from a nucleotide sequence selected from the group consisting of SEQ ID NOs:1, 3, 5, 7, 9, 11, 13, 15, 17, 19, 21, 23, 25, 27, 29, and 31, and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated suitable host cell with a chimeric gene or isolated polynucleotide of the present invention.

In a seventh embodiment, the invention concerns a biotin synthase polypeptide of at least 52 amino acids comprising at least 85% identity based on the Clustal method of alignment compared to a polypeptide selected from the group consisting of SEQ ID NOs:2, 4, 6, 8, 10, 12, 14, and 16, or preferably a biotin synthase polypeptide of at least 100 amino acids comprising at least 85% identity based on the Clustal method of alignment compared to a polypeptide selected from the group consisting of SEQ ID NOs:18, 20, 22, 24, 26, 28, 30, and 32.

In an eighth embodiment, the invention relates to a method of selecting an isolated polynucleotide that affects the level of expression of a biotin synthase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the biotin synthase polypeptide or enzyme activity in the host cell containing the isolated polynucleotide; and (d) comparing the level of the biotin synthase polypeptide or enzyme activity in the host cell containing the isolated polynucleotide with the level of the biotin synthase polypeptide or enzyme activity in the host cell that does not contain the isolated polynucleotide.

In a ninth embodiment, the invention concerns a method of obtaining a nucleic acid fragment encoding a substantial portion of a biotin synthase polypeptide, preferably a plant biotin synthase polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, 29, and 31, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a biotin synthase amino acid sequence.

In a tenth embodiment, this invention relates to a method of obtaining a nucleic acid fragment encoding all or a substantial portion of the amino acid sequence encoding a biotin synthase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the biotin synthase polynucleotide in an amount sufficient to complement a null mutant to provide a positive selection means.

In a thirteenth embodiment, this invention relates to a method of altering the level of expression of a biotin synthase in a host cell comprising: (a) transforming a host cell with a chimeric gene of the present invention; and (b) growing the transformed host cell under conditions that are suitable for expression of the chimeric gene wherein expression of the chimeric gene results in production of altered levels of the biotin synthase in the transformed host cell.

A further embodiment of the instant invention is a method for evaluating at least one compound for its ability to inhibit the activity of a biotin synthase, the method comprising the steps of: (a) transforming a host cell with a chimeric gene comprising a nucleic acid fragment encoding a biotin synthase polypeptide, operably linked to suitable regulatory sequences; (b) growing the transformed host cell under conditions that are suitable for expression of the chimeric gene wherein expression of the chimeric gene results in production of biotin in the transformed host cell; (c) optionally purifying the biotin synthase polypeptide expressed by the transformed host cell; (d) treating the biotin synthase polypeptide with a compound to be tested; and (e) comparing the activity of the biotin synthase polypeptide that has been treated with a test compound to the activity of an untreated biotin synthase polypeptide, thereby selecting compounds with potential for inhibitory activity.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A, 1B, and 1C shows a comparison of the amino acid sequences of the barley (SEQ ID NO:18), corn (SEQ ID NOs:20, 22, and 24), prickly poppy (SEQ ID NO:26), soybean (SEQ ID NOs:28 and 30), and wheat (SEQ ID NO:32) biotin synthase polypeptides to the enzymes from *Arabidopsis thaliana* (1705463, SEQ ID NO:33), fission yeast (*Schizosaccharomyces pombe*, 2995363, SEQ ID NO:34), and yeast (*Saccharomyces cerevisiae*, 6321725, SEQ ID NO:35). The conserved iron binding consensus sequence (GXCXEDCXYCXQ) is highlighted in italics and underlined (SEQ ID NO:36).

FIG. 2 shows a comparison of the sequences from nucleotides 301–441 of clone cdt2c.pk002.c17:fis (SEQ ID NO:19) and the comparable region (nucleotides 253–492) of clone cho1c.pk009.j14:fis (SEQ ID NO:21). The SEQ ID NO:19 sequence has a 99 nucleotide "deletion" from this region with respect to the SEQ ID NO:21 sequence. This region encompasses the conserved iron binding sequence noted in FIG. 1. The "deleted" sequence shown in SEQ ID NO 21 has consensus intron border sequences (GT . . . AG) and the two sequences may represent alternative splice products of the same precursor.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Biotin Synthase

| | | SEQ ID NO: | |
|---|---|---|---|
| Protein | Clone Designation | (Nucleotide) | (Amino Acid) |
| barley [*Hordeum vulgare*] | bsh1.pk0005.d10 | 1 | 2 |
| maize [*Zea mays*] | cdt2c.pk002.c17 | 3 | 4 |
| maize [*Zea mays*] | cho1c.pk009.j14 | 5 | 6 |
| maize [*Zea mays*] | Contig of: | | |
| | cca.pk0012.g11 | 7 | 8 |
| | cco1n.pk069.f1 | | |
| | p0004.cb1hi70r | | |
| | p0041.crtax65r | | |
| | p0094.cssth33r | | |
| | p0094.cssth33ra | | |
| prickly poppy [*Argemone mexicana*] | pps1c.pk008.m8 | 9 | 10 |
| soybean [*Glycine max*] | Contig of: | | |
| | sah1c.pk001.b19 | 11 | 12 |
| | sfl1.pk128.m2 | | |
| | sgc5c.pk001.j23 | | |
| | sgs2c.pk003.p6 | | |
| | sr1.pk0026.d1 | | |
| | src2c.pk025.k23 | | |
| | ssm.pk0072.h10 | | |
| soybean [*Glycine max*] | sls2c.pk010.l24 | 13 | 14 |
| wheat-common [*Triticum aestivum*] | wr1.pk0104.b6 | 15 | 16 |
| barley [*Hordeum vulgare*] | bsh1.pk0005.d10 | 17 | 18 |
| maize [*Zea mays*] | cdt2c.pk002.c17 | 19 | 20 |
| maize [*Zea mays*] | cho1c.pk009.j14 | 21 | 22 |
| maize [*Zea mays*] | cca.pk0012.g11:fis | 23 | 24 |
| prickly poppy [*Argemone mexicana*] | pps1c.pk008.m8:fis | 25 | 26 |
| soybean [*Glycine max*] | sgc5c.pk001.j23:fis | 27 | 28 |
| soybean [*Glycine max*] | Contig of: | | |
| | sls1c.pk015.d12 | 29 | 30 |
| | sls2c.pk010.l24:fis | | |
| wheat-common [*Triticum aestivum*] | wr1.pk0104.b6:fis | 31 | 32 |

The Sequence Listing contains the one letter code for nucleotide sequence characters and the three letter codes for amino acids as defined in conformity with the IUPAC-IUJBMB standards described in *Nucleic Acids Res.* 13:3021–3030 (1985) and in the *Biochemical J* 219 (No. 2):345–373 (1984) which are herein incorporated by reference. The symbols and format used for nucleotide and amino acid sequence data comply with the requirements of 37 C.F.R. §1.822.

DETAILED DESCRIPTION OF THE INVENTION

In the context of this disclosure, a number of terms shall be utilized. The terms "polynucleotide," "polynucleotide sequence," "nucleic acid sequence," and "nucleic acid fragment"/"isolated nucleic acid fragment" are used interchangeably. These terms encompass nucleotide sequences and the like. A polynucleotide may be an RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7, 9, 11, 13, 15, 17, 19, 21, 23, 25, 27, 29, and 31, or the complement of such sequences.

The term "isolated" refers to materials, such as nucleic acid molecules and/or proteins, which are substantially free from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping sequences. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence, to form a "contig".

As used herein, "substantially similar," in the case of nucleic acid fragments, refers to changes in one or more nucleotide bases that result in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to alter gene expression patterns by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

In one embodiment, substantially similar nucleic acid fragments may be obtained by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, 29, and 31, and the complement of such nucleotide sequences may be used in methods of selecting an isolated polynucleotide that affects the expression of a biotin synthase polypeptide in a host cell. A method of selecting an isolated polynucleotide that affects the level of expression of a polypeptide in a virus or in a host cell (eukaryotic, such as a plant cell or a yeast cell, or prokaryotic such as a bacterial cell) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art.

Suitable nucleic acid fragments (isolated polynucleotides of the present invention) encode polypeptides that are at least about 80% identical, preferably at least about 85%, more preferably at least about 90%, still more preferably at least about 95%, and most preferably at least about 98% identical to the amino acid sequences reported herein.

Suitable nucleic acid fragments not only have the above identities but typically encode a polypeptide having at least 20, preferably 40, more preferably 50, still more preferably 80, more preferably at least 100, more preferably at least 150 amino acids, preferably at least 200 amino acids, more preferably at least 250 amino acids, still more preferably at least 300 amino acids, again more preferably at least 350 amino acids, and most preferably at least 400 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of lose sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell. "Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.*

42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 52 amino acids having at least 85% identity based on the Clustal method of alignment when compared to a polypeptide selected from the group consisting of SEQ ID NOs:2, 4, 6, 8, 10, 12, 14, and 16, or preferably a polypeptide of at least 100 amino acids having at least 85% identity based on the Clustal method of alignment when compared to a polypeptide selected from the group consisting of SEQ ID NOs:18, 20, 22, 24, 26, 28, 30, and 32, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, 11, 13, 15, 17, 19, 21, 23, 25, 27, 29, and 31, that codes for the polypeptide selected from the group consisting of SEQ ID NOs:2, 4, 6, 8, 10, 12, 14, and 16.

Nucleic acid fragments encoding at least a portion of several biotin synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other biotin synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci.* USA 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci.* USA 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably one of at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, 29, and 31, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a biotin synthase polypeptide, preferably a substantial portion of a plant biotin synthase polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, 29, and 31, and the complement of such nucleotide sequences; and amplifying a nucleic acid fragment (preferably a cDNA inserted in a cloning vector) using the oligonucleotide primer. The amplified nucleic acid fragment preferably will encode a portion of a biotin synthase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, a yeast cell, a bacterial cell, and a plant cell.

As was noted above, the nucleic acid fragments of the instant invention may be used to create transgenic plants in which the disclosed polypeptides are overexpressed, or their expression is suppressed, in various cell types or developmental stages. This would have the effect of altering the level of biotin in those cells. Biotin synthase could also be used as a target for herbicides since the loss of the enzyme leads to and embryo-defective phenotype (Patton et al. (1998) *Plant Physiol* 116: 935–946). Altering the levels of biotin synthase in cells could make them more or less susceptible to herbicidal compounds.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The skilled artisan readily recognizes that the choice of plasmid vector is dependent upon many factors, such as whether the vector is for protein expression, gene-overexpression or suppression, and in what type of host cell the vectors are propagated. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 52 amino acids that has at least 85% identity based on the Clustal method of alignment when compared to a polypeptide selected from the group consisting of SEQ ID NOs:2, 4, 6, 8, 10, 12, 14, and 16, or preferably a polypeptide of at least 100 amino acids that has at least 85% identity based on the Clustal method of alignment when compared to a polypeptide selected from the group consisting of SEQ ID NOs:18, 20, 22, 24, 26, 28, 30, and 32.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded biotin synthases. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyze various steps in biotin biosynthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides.

Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adapter. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various barley, corn, prickly poppy, soybean, and wheat tissues were prepared. The characteristics of the libraries are described below.

TABLE 2 cDNA Libraries from Barley, Corn, Prickly Poppy, Soybean, and Wheat

| Library | Tissue | Clone |
|---|---|---|
| bsh1 | Barley Sheath, Developing Seedling | bsh1.pk0005.d10 |
| cdt2c | Corn (Zea mays L.) developing tassel 2 | cdt2c.pk002.c17 |
| cho1c | Corn (Zea mays L., Alexho Synthetic High Oil) embryo 20 DAP | cho1c.pk009.j14 |
| p0094 | Leaf collars for the Ear leaf, screened 1 (EL) and the next leaf above and below the EL Growth conditions: field; control or untreated tissues | p0094.cssth33r |
| pps1c | Prickly poppy developing seeds | pps1c.pk008.m8 |
| sgc5c | Soybean (Glycine max L., Wye) germinating cotyledon (¾yellow; 15-24 DAG) | sgc5c.pk001.j23 |
| sls1c | Soybean (Glycine max L., S1990) infected with Sclerotinia sclerotiorum mycelium. | sls1c.pk015.d12 |
| sls2c | Soybean (Glycine max L., Manta) infected with Sclerotinia sclerotiorum mycelium | sls2c.pk010.124 |
| wr1 | Wheat Root From 7 Day Old Seedling | wr1.pk0104.b6 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding biotin synthases were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Biotin Synthase

The BLASTX search using the EST sequences from clones listed in Table 3 revealed similarity of the polypeptides encoded by the cDNAs to biotin synthase from *Arabidopsis thaliana* and fission yeast (*Schizosaccharomyces pombe*) (NCBI Accession No. gi 1705463 and gi 2995363, respectively). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Biotin Synthase

| Clone | Status | Accession No. | BLAST pLog Score |
|---|---|---|---|
| bsh1.pk0005.d10 | EST | 1705463 | 56.20 |
| cdt2c.pk002.c17 | EST | 1705463 | 25.30 |
| cho1c.pk009.j14 | EST | 1705463 | 32.30 |
| Contig of: | Contig | 1705463 | 254.00 |
| cca.pk0012.g11 | | | |
| cco1n.pk069.f1 | | | |
| p0004.cb1hi70r | | | |
| p0041.crtax65r | | | |
| p0094.cssth33r | | | |
| p0094.cssth33ra | | | |
| pps1c.pk008.m8 | EST | 1705463 | 52.50 |
| Contig of: | Contig | 1705463 | 254.00 |
| sah1c.pk001.b19 | | | |
| sfl1.pk128.m2 | | | |
| sgc5c.pk001.j23 | | | |
| sgs2c.pk003.p6 | | | |
| sr1.pk0026.d1 | | | |
| src2c.pk025.k23 | | | |
| ssm.pk0072.h10 | | | |
| sls2c.pk010.124 | EST | 2995363 | 18.70 |
| wr1.pk0104.b6 | EST | 1705463 | 34.70 |

The sequence of the entire cDNA insert in the clones listed in Table 3 was determined. Further sequencing and searching of the DuPont proprietary database allowed the identification of other corn, rice, soybean and/or wheat clones encoding biotin synthase. The BLASTX search using the EST sequences from clones listed in Table 4 revealed similarity of the polypeptides encoded by the cDNAs to biotin synthase from *Arabidopsis thaliana* and yeast (*Saccharomyces cerevisiae*) (NCBI Accession No. gi 1705463 and gi 6321725, respectively). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Biotin Synthase

| Clone | Status | Accession No. | BLAST pLog Score |
|---|---|---|---|
| bsh1.pk0005.d10:fis | FIS | 1705463 | 180.00 |
| cdt2c.pk002.c17:fis | FIS | 1705463 | 152.00 |
| cho1c.pk009.j14:fis | FIS | 1705463 | 179.00 |
| cca.pk0012.g11:fis | FIS | 1705463 | 178.00 |
| pps1c.pk008.m8:fis | FIS | 1705463 | 180.00 |
| sgc5c.pk001.j23:fis | FIS | 1705463 | 180.00 |
| Contig of: | | | |
| sls1c.pk015.d12 | Contig | 6321725 | 119.00 |
| sls2c.pk010.124:fis | | | |
| wr1.pk0104.b6:fis | FIS | 1705463 | 127.00 |

FIGS. 1A–1C shows a comparison of the amino acid sequences of the barley (SEQ ID NO:18), corn (SEQ ID NOs:20, 22, and 24), prickly poppy (SEQ ID NO:26), soybean (SEQ ID NOs:28 and 30), and wheat (SEQ ID NO:32) biotin synthase polypeptides to the enzymes from *Arabidopsis thaliana* (1705463, SEQ ID NO:33), fission yeast (*Schizosaccharomyces pombe*, 2995363, SEQ ID NO:34), and yeast (*Saccharomyces cerevisiae*, 6321725, SEQ ID NO:35). The conserved iron binding consensus sequence (GXCXEDCXYCXQ) is highlighted in italics and underlined (SEQ ID NO:36). The sequence for clone cdt2c.pk002.c17 (SEQ ID NOs:3,4 and 19,20) is very similar to the other two corn biotin synthase sequences with the exception of a 99 nucleotide deletion (33 amino acids) which includes the iron binding consensus motif (see FIGS. 1A–1C and 2). It is very likely that this cDNA clone represents a splice variant of the mRNA represented in SEQ ID NO:21. The deleted sequence has consensus GT . . . AG intron border sequences, and the surrounding sequences fall within the requirements for a functional splice site junction. Whether this alternative splice product has any biological or regulatory role within the plant is unknown at this time. The second soybean sequence (SEQ ID NOs:13, 14 and 29,30) is the only one analyzed in this group that shows higher homology to yeast biotin synthase genes than to plant biotin synthase sequences. The cDNA libraries that these clones were isolated from (sls1c, sls2c) were soybean tissues infected with the fungus Sclerotinia. It can not be ruled out that, this clone may represent a fungal rather than plant biotin synthase sequence.

The data in Table 5 represents a calculation of the percent identity of the amino acid sequences set forth in SEQ ID NOs:2, 4, 6, 8, 10, 12, 14, 16, 18, 20, 22, 24, 26, 28, 30, and 32, and the *Arabidopsis thaliana* and fission yeast (*Schizosaccharomyces pombe*) (NCBI Accession No. gi 1705463 and gi 2995363, respectively and SEQ ID NO:33 and 34).

TABLE 5

Percent Identity of Amino Acid Sequences Deduced From the Nucleotide Sequences of cDNA Clones Encoding Polypeptides Homologous to Biotin Synthase

| SEQ ID NO. | Percent Identity to 1705463 | Percent Identity to 2995363 |
| --- | --- | --- |
| 2 | 71.5% | |
| 4 | 53.9% | |
| 6 | 68.4% | |
| 8 | 83.1% | |
| 10 | 72.3% | |
| 12 | 80.2% | |
| 14 | | 65.4% |
| 16 | 83.3% | |
| 18 | 79.4% | |
| 20 | 77.3% | |
| 22 | 79.8% | |
| 24 | 79.6% | |
| 26 | 82.3% | |
| 28 | 79.9% | |
| 30 | | 54.5% |
| 32 | 81.7% | |

Sequence alignments and percent identity calculations were performed using the Megalign program of the LASERGENE bioinformatics computing suite (DNASTAR Inc., Madison, Wis. Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a biotin synthase. These sequences represent the first monocot, corn, soybean, wheat, and prickly poppy sequences encoding biotin synthase known to Applicant.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XLI-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 m in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/ He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS- 1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the gluphosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the D subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl₂ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adapter containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Biotin Synthase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under experimental conditions which permit optimal enzymatic activity. For example, assays for biotin synthase are presented by Birch et al. (1995) J Biol Chem 270:19158–19165.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having biotin synthase activity, wherein the amino acid sequence of the polypeptide and the amino acid sequence of SEQ ID NO:22 or 24 have at least 85% sequence identity based on the Clustal alignment method, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:22 or 24 have at least 90% sequence identity based on the Clustal alignment method.

3. The polynucleotide of claim 1, wherein the amino acid sequence of the polypeptide and the amino acid sequence of SEQ ID NO:22 or 24 have at least 95% sequence identity based on the Clustal alignment method.

4. The polynucleotide of claim 1 wherein the polypeptide comprises the amino acid sequence of SEQ ID NO:22 or 24.

5. The polynucleotide of claim 1, wherein the nucleotide sequence comprises the nucleotide sequence of SEQ ID NO:21 or 23.

6. A host cell comprising the polynucleotide of claim 1.

7. The cell of claim 6, wherein the cell is selected from the group consisting of a yeast cell, a bacterial cell and a plant cell.

8. A transgenic plant comprising the polynucleotide of claim 1.

9. A method for transforming a cell comprising introducing into a cell the polynucleotide of claim 1.

10. A method for producing a transgenic plant, comprising
    (a) transforming a plant cell with the polynucleotide of claim 1, and
    (b) regenerating a plant from the transformed plant cell.

11. A chimeric gene comprising the polynucleotide of claim 1 operably linked to at least one suitable regulatory sequence.

12. A vector comprising the polynucleotide of claim 1.

13. A seed comprising the chimeric gene of claim 11.

* * * * *

SEQUENCE LISTING

<160> NUMBER OF SEQ ID NOS: 36

<210> SEQ ID NO 1
<211> LENGTH: 512
<212> TYPE: DNA
<213> ORGANISM: Hordeum vulgare
<220> FEATURE:
<221> NAME/KEY: Unsure
<222> LOCATION: (94)..(94)
<223> OTHER INFORMATION: n = A, C, G, or T
<221> NAME/KEY: Unsure
<222> LOCATION: (460)..(460)
<223> OTHER INFORMATION: n = A, C, G, or T
<221> NAME/KEY: Unsure
<222> LOCATION: (462)..(462)
<223> OTHER INFORMATION: n = A, C, G, or T

<400> SEQUENCE: 1

```
caactccctc ggcagtatcg cctagtgcag cagcggctcc gttccggcca gctttgctcg      60
ccgagccggc catgatgctg ctgctcgcgc gcancttcgc tcccgcgtcc ggtcccccttt    120
cgcctccgcc gttagcgccg cgccttctc atcggtatcg gcggccgcgg cggaggcgga     180
cgggcggtgc gggacgggcc caggaacgac tggacccgcc ccgagatcca ggccatctac    240
gactccccgc tcctcgacct cctcttccac ggggctcaag tccataggaa tgtccataaa    300
tttagagaag tgcaacaatg cacacttctt tcaataaaga ctggtgggtg cagcgaagat    360
tgttcatact gcccacagtc ttcaagatac agtaccggat tgaaggctga aaaattaatg    420
aagaaagatg ccgtcctaga agcagctaaa aaggcaaagn angctgggag cacccgattt    480
tgattggagc gatggagaga gacaattggc ag                                  512
```

<210> SEQ ID NO 2
<211> LENGTH: 137
<212> TYPE: PRT
<213> ORGANISM: Hordeum vulgare
<220> FEATURE:
<221> NAME/KEY: UNSURE
<222> LOCATION: (131)..(131)
<223> OTHER INFORMATION: Xaa = any amino acid

<400> SEQUENCE: 2

```
Met Met Leu Leu Leu Ala Arg Ser Leu Arg Ser Arg Val Arg Ser Pro
  1               5                  10                  15

Phe Ala Ser Ala Val Ser Ala Ala Pro Phe Ser Ser Val Ser Ala Ala
                 20                  25                  30

Ala Ala Glu Ala Glu Arg Ala Val Arg Asp Gly Pro Arg Asn Asp Trp
             35                  40                  45

Thr Arg Pro Glu Ile Gln Ala Ile Tyr Asp Ser Pro Leu Leu Asp Leu
     50                  55                  60

Leu Phe His Gly Ala Gln Val His Arg Asn Val His Lys Phe Arg Glu
 65                  70                  75                  80

Val Gln Gln Cys Thr Leu Leu Ser Ile Lys Thr Gly Gly Cys Ser Glu
                 85                  90                  95
```

```
Asp Cys Ser Tyr Cys Pro Gln Ser Ser Arg Tyr Ser Thr Gly Leu Lys
                100                 105                 110

Ala Glu Lys Leu Met Lys Lys Asp Ala Val Leu Glu Ala Ala Lys Lys
            115                 120                 125

Ala Lys Xaa Ala Gly Ser Thr Arg Phe
        130                 135

<210> SEQ ID NO 3
<211> LENGTH: 496
<212> TYPE: DNA
<213> ORGANISM: Zea mays
<220> FEATURE:
<221> NAME/KEY: Unsure
<222> LOCATION: (33)..(33)
<223> OTHER INFORMATION: n = A, C, G, or T
<221> NAME/KEY: Unsure
<222> LOCATION: (318)..(318)
<223> OTHER INFORMATION: n = A, C, G, or T
<221> NAME/KEY: Unsure
<222> LOCATION: (321)..(321)
<223> OTHER INFORMATION: n = A, C, G, or T
<221> NAME/KEY: Unsure
<222> LOCATION: (365)..(365)
<223> OTHER INFORMATION: n = A, C, G, or T
<221> NAME/KEY: Unsure
<222> LOCATION: (446)..(446)
<223> OTHER INFORMATION: n = A, C, G, or T

<400> SEQUENCE: 3
tccaatcggg tgggcagttt ttaaggaaac canggaccgc aagcaagcaa gccgccccag      60
ccgacgaggc gaggagcgtg caattccgta gctgcaacga actccctcga ccgtatcgcc    120
cgctgctcct ctatcccttt cctgctgctg ctactacctt aagctatcac tatcatggcc    180
ttgatgctgc tagcgcgcaa cctgcgctcc cgcctccgcc accgctcgc cgccgccgcg    240 gggttctcgt cggccgcggc ggaggcggag agggcgatac gggacgggcc gcggaacgac    300
tggagccggc ccgagatnca ngccgtctac gactcaccgc tcctcgacct cctctttcac    360
ggggntcagt catcaagata caacactgga ttgaagggcc aaaaattgat gaacaaatat    420
gctgtcttgg gagcagcaaa aaaggnaaaa gagtctggga agcaaccgtt tttgcatggg    480
aactgcattg gagaaa                                                    496

<210> SEQ ID NO 4
<211> LENGTH: 102
<212> TYPE: PRT
<213> ORGANISM: Zea mays
<220> FEATURE:
<221> NAME/KEY: UNSURE
<222> LOCATION: (48)..(49)
<223> OTHER INFORMATION: Xaa = any amino acid
<221> NAME/KEY: UNSURE
<222> LOCATION: (64)..(64)
<223> OTHER INFORMATION: Xaa = any amino acid
<221> NAME/KEY: UNSURE
<222> LOCATION: (91)..(91)
<223> OTHER INFORMATION: Xaa = any amino acid

<400> SEQUENCE: 4

Met Ala Leu Met Leu Leu Ala Arg Asn Leu Arg Ser Arg Leu Arg Pro
1               5                   10                  15

Pro Leu Ala Ala Ala Ala Gly Phe Ser Ser Ala Ala Ala Glu Ala Glu
            20                  25                  30

Arg Ala Ile Arg Asp Gly Pro Arg Asn Asp Trp Ser Arg Pro Glu Xaa
        35                  40                  45

Xaa Ala Val Tyr Asp Ser Pro Leu Leu Asp Leu Leu Phe His Gly Xaa
    50                  55                  60
```

```
Gln Ser Ser Arg Tyr Asn Thr Gly Leu Lys Gly Gln Lys Leu Met Asn
 65                  70                  75                  80

Lys Tyr Ala Val Leu Gly Ala Ala Lys Lys Xaa Lys Glu Ser Gly Lys
                 85                  90                  95

Gln Pro Phe Leu His Gly
            100
```

<210> SEQ ID NO 5
<211> LENGTH: 497
<212> TYPE: DNA
<213> ORGANISM: Zea mays
<220> FEATURE:
<221> NAME/KEY: Unsure
<222> LOCATION: (192)..(192)
<223> OTHER INFORMATION: n = A, C, G, or T
<221> NAME/KEY: Unsure
<222> LOCATION: (460)..(460)
<223> OTHER INFORMATION: n = A, C, G, or T
<221> NAME/KEY: Unsure
<222> LOCATION: (463)..(463)
<223> OTHER INFORMATION: n = A, C, G, or T
<221> NAME/KEY: Unsure
<222> LOCATION: (469)..(469)
<223> OTHER INFORMATION: n = A, C, G, or T
<221> NAME/KEY: Unsure
<222> LOCATION: (490)..(490)
<223> OTHER INFORMATION: n = A, C, G, or T

<400> SEQUENCE: 5

```
agccgacgag gcgaggagcg tgcaattccg tagctgcaac tgcaacgaac tccctccctc    60
cctcgaccgt atcgcccgct gctcctctat ccctttcctg ctgctgctac taccttaagc   120
tatcatggcc ttgatgctgc tagcgcgcaa cctgcgctcc cgcctccgcc caccgctcgc   180
cgccgccgcg gngttctcgt cggccgcggc ggaggcggag agggcgatac gggacgggcc   240
gcggaacgac tggagccggc ccgagattca agccgtctac gactcaccgc tcctcgacct   300
cctctttcac ggggctcaag tccacagaaa tgtccataaa ttcaagagaa gtgcagcaat   360
gcacacttct ttcaatcaag actggtggga tgcagtgaag attgttctta ctgtcctcaa   420
gtcatcaaag aatacaacac tgggattgaa gggcccaaan aanttgatna acaaaagatg   480
ctgtcttggn aacaaca                                                  497
```

<210> SEQ ID NO 6
<211> LENGTH: 98
<212> TYPE: PRT
<213> ORGANISM: Zea mays
<220> FEATURE:
<221> NAME/KEY: UNSURE
<222> LOCATION: (23)..(23)
<223> OTHER INFORMATION: Xaa = any amino acid
<221> NAME/KEY: UNSURE
<222> LOCATION: (72)..(72)
<223> OTHER INFORMATION: Xaa = any amino acid
<221> NAME/KEY: UNSURE
<222> LOCATION: (89)..(89)
<223> OTHER INFORMATION: Xaa = any amino acid

<400> SEQUENCE: 6

```
Met Ala Leu Met Leu Leu Ala Arg Asn Leu Arg Ser Arg Leu Arg Pro
  1               5                  10                  15

Pro Leu Ala Ala Ala Ala Xaa Phe Ser Ser Ala Ala Ala Glu Ala Glu
                 20                  25                  30

Arg Ala Ile Arg Asp Gly Pro Arg Asn Asp Trp Ser Arg Pro Glu Ile
                 35                  40                  45

Gln Ala Val Tyr Asp Ser Pro Leu Leu Asp Leu Leu Phe His Gly Ala
```

```
                50                  55                  60
Gln Val His Arg Asn Val His Xaa Ser Arg Glu Val Gln Gln Cys Thr
 65                  70                  75                  80

Leu Leu Ser Ile Lys Thr Gly Gly Xaa Ser Glu Asp Cys Ser Tyr Cys
                 85                  90                  95

Pro Gln

<210> SEQ ID NO 7
<211> LENGTH: 1152
<212> TYPE: DNA
<213> ORGANISM: Zea mays

<400> SEQUENCE: 7
gcagccgacg aggcgaggag cgtgcaattc cgtagctgca acgaactccc tcgaccgtat      60
cgcccgctgc tcctctatcc ctttcctgct gctgctacta ccttaagcta tcactatcat     120
ggccttgatg ctgctagcgc gcaacctgcg ctcccgcctc cgcccaccgc tcgccgccgc     180
cgcggcgttc tcgtcggccg cggcggaggc ggagagggcg atacgggacg gccgcggaa      240
cgactggagc cggcccgaga tccaggccgt ctacgactca ccgctcctcg acctcctctt     300
tcacggggct caggtccaca gaaatgtcca taaattcaga gaagtgcagc aatgcacact     360
tctttcaatc aagactggtg gatgcagtga agattgttct tactgtcctc agtcatcaag     420
atacaacact ggattgaagg cccaaaaatt gatgaacaaa tatgctgtct tggaagcagc     480
aaaaaaggca aaagagtctg ggagcacccg ttttttgcatg ggagctgcat ggagagaaac    540
cattggcagg aaatcaaact tcaaccagat tcttgaatat gtcaaggaaa taagggggtat   600
gggcatggag gtctgttgca cactaggcat gatagagaaa caacaagctg aagaactcaa    660
gaaggctgga cttacagcat ataatcataa cctagataca tcaagagagt attatcccaa    720
cattattacc acaagatcat atgatgatag actgcagact cttgagcatg tccgtgaagc    780
tggaataagc atctgctcag gtggaatcat tggtcttggt gaagcagagg aggaccgggt    840
agggttgttg catacccctag ctaccttgcc tacacaccca gagagcgttc ctattaatgc    900
attggttgct gtaaaaggca cacctcttga ggaccagaag cctgtagaga tctgggaaat    960
gatccgcatg atcgccactg ctcggatcac gatgccaaag caatggtga ggctttcagc   1020
aggccgagta cggttctcga tgccagaaca agcgctgtgc ttcctcgctg ggccaactc    1080
catccttgcc ggcgagaaac ttctcacaac cgcaaacaac gactttgatg cggaccaagc   1140
gatgttcaag at                                                         1152

<210> SEQ ID NO 8
<211> LENGTH: 344
<212> TYPE: PRT
<213> ORGANISM: Zea mays

<400> SEQUENCE: 8

Met Ala Leu Met Leu Leu Ala Arg Asn Leu Arg Ser Arg Leu Arg Pro
  1               5                  10                  15

Pro Leu Ala Ala Ala Ala Ala Phe Ser Ser Ala Ala Glu Ala Glu
                 20                  25                  30

Arg Ala Ile Arg Asp Gly Pro Arg Asn Asp Trp Ser Arg Pro Glu Ile
                 35                  40                  45

Gln Ala Val Tyr Asp Ser Pro Leu Leu Asp Leu Leu Phe His Gly Ala
                 50                  55                  60

Gln Val His Arg Asn Val His Lys Phe Arg Glu Val Gln Gln Cys Thr
 65                  70                  75                  80
```

```
Leu Leu Ser Ile Lys Thr Gly Gly Cys Ser Glu Asp Cys Ser Tyr Cys
                85                  90                  95

Pro Gln Ser Ser Arg Tyr Asn Thr Gly Leu Lys Ala Gln Lys Leu Met
            100                 105                 110

Asn Lys Tyr Ala Val Leu Glu Ala Ala Lys Lys Ala Lys Glu Ser Gly
        115                 120                 125

Ser Thr Arg Phe Cys Met Gly Ala Ala Trp Arg Glu Thr Ile Gly Arg
    130                 135                 140

Lys Ser Asn Phe Asn Gln Ile Leu Glu Tyr Val Lys Glu Ile Arg Gly
145                 150                 155                 160

Met Gly Met Glu Val Cys Cys Thr Leu Gly Met Ile Glu Lys Gln Gln
                165                 170                 175

Ala Glu Glu Leu Lys Lys Ala Gly Leu Thr Ala Tyr Asn His Asn Leu
            180                 185                 190

Asp Thr Ser Arg Glu Tyr Tyr Pro Asn Ile Ile Thr Thr Arg Ser Tyr
        195                 200                 205

Asp Asp Arg Leu Gln Thr Leu Glu His Val Arg Glu Ala Gly Ile Ser
    210                 215                 220

Ile Cys Ser Gly Gly Ile Ile Gly Leu Gly Glu Ala Glu Glu Asp Arg
225                 230                 235                 240

Val Gly Leu Leu His Thr Leu Ala Thr Leu Pro Thr His Pro Glu Ser
                245                 250                 255

Val Pro Ile Asn Ala Leu Val Ala Val Lys Gly Thr Pro Leu Glu Asp
            260                 265                 270

Gln Lys Pro Val Glu Ile Trp Glu Met Ile Arg Met Ile Ala Thr Ala
        275                 280                 285

Arg Ile Thr Met Pro Lys Ala Met Val Arg Leu Ser Ala Gly Arg Val
    290                 295                 300

Arg Phe Ser Met Pro Glu Gln Ala Leu Cys Phe Leu Ala Gly Ala Asn
305                 310                 315                 320

Ser Ile Leu Ala Gly Glu Lys Leu Leu Thr Thr Ala Asn Asn Asp Phe
                325                 330                 335

Asp Ala Asp Gln Ala Met Phe Lys
            340

<210> SEQ ID NO 9
<211> LENGTH: 562
<212> TYPE: DNA
<213> ORGANISM: Argemone mexicana
<220> FEATURE:
<221> NAME/KEY: Unsure
<222> LOCATION: (553)..(553)
<223> OTHER INFORMATION: n = A, C, G, or T

<400> SEQUENCE: 9
cattcgagaa ataaagagct gtaaaatttt tagggttttt ctgcataact ctacactcga      60
agcttcatca atagaaatat cataaacaga agaattcaaa atgcttaaag ttcaatcttt     120
gagagctcgt cttcgacctt tgattttcat ttctacattt tcttctctct catcatcttc     180
ttcttcttca gctgctgctg ttcaagcaga agaacgatt  aaagaaggtc caagaaacga     240
ttggagcaga gatgaaatta atcggtttta tgattctcca gttctcgatc ttctcttcca     300
tgcagctcaa gtccatagac atgctcacaa cttcaggaa  gtgcagcaat gtactcttct     360
ctctgttaag acaggtgggt gcagtgaaga ttgttcatat tgtccacaat cttccaggta     420
tgacactgga gtgaaagccc aaaagctgat gaacaaggga cgcagttctg caaggaagca     480
```

```
agaaaaggca aaggaggcgg ggtagtacac gttttcgcaa tggtggctgc aatggggaga      540
tacaatgggg aangaagaac aa                                              562
```

<210> SEQ ID NO 10
<211> LENGTH: 119
<212> TYPE: PRT
<213> ORGANISM: Argemone mexicana

<400> SEQUENCE: 10

```
Met Leu Lys Val Gln Ser Leu Arg Ala Arg Leu Arg Pro Leu Ile Phe
1               5                   10                  15

Ile Ser Thr Phe Ser Ser Leu Ser Ser Ser Ser Ser Ala Ala
            20                  25                  30

Ala Val Gln Ala Glu Arg Thr Ile Lys Glu Gly Pro Arg Asn Asp Trp
            35                  40                  45

Ser Arg Asp Glu Ile Lys Ser Val Tyr Asp Ser Pro Val Leu Asp Leu
        50                  55                  60

Leu Phe His Ala Ala Gln Val His Arg His Ala His Asn Phe Arg Glu
65                  70                  75                  80

Val Gln Gln Cys Thr Leu Leu Ser Val Lys Thr Gly Gly Cys Ser Glu
                85                  90                  95

Asp Cys Ser Tyr Cys Pro Gln Ser Ser Arg Tyr Asp Thr Gly Val Lys
            100                 105                 110

Ala Gln Lys Leu Met Asn Lys
        115
```

<210> SEQ ID NO 11
<211> LENGTH: 1340
<212> TYPE: DNA
<213> ORGANISM: Glycine max

<400> SEQUENCE: 11

```
ctagtactgc tccctctgcg acttcgtttc gtagagggat tttggccgcc aaataaacag       60
tctcaccata aactccaaag tcccaacgct aaacgaaacc aaaccccaaa cacaaatacc      120
gttgttgtct gttgtctctg tcgtgtctat attcgcagat ctctcactca ttctctgttg      180
tttctctgcc caacttcgaa ttcgaaagca aaacatgtt tttggcgaga cccattttcc       240
gagcaccctc cctttgggcg ttgcactctt cctacgcgta ttcctctgcc tcagcagctg      300
caattcaagc tgagagagcc atcaaagaag gacccagaaa cgattggagc gagaccaag       360 tcaaatccat ctcgactct cccattctcg atcttctctt ccatgggct caagttcaca       420 gacatgctca aacttcagg gaagttcaac agtgtactct tctgtctatc aaaacaggag      480
ggtgcagtga agattgttcc tattgtcctc aatcctctaa gtatgataca ggagtcaaaa      540
ggccaagcct tatgaacaag gaagctgttc tccaggctgc aaagaaggca aaagaggctg      600
ggagcactcg cttttgtatg ggtgctgcgt ggagggatac actaggaaga aagaccaact      660
tcaaccagat ccttgaatat gtgaaagaca agggacat gggaatggag gtttgttgca      720
cccttggcat gctggagaaa cagcaggctg ttgaactcaa gaaggcaggt ctcactgctt      780
ataatcacaa tcttgacact tcaagggagt attatccaaa cataatcaca acaaggactt      840
atgatgagcg tcttcaaacc cttgagtttg ttcgggatgc agggatcaat gtttgttctg      900
gaggaattat agggcttgga gaagcagagg aggatcgtgt aggtttgtta catacattgt      960
caacacttcc cacccatcca gagagtgttc ctattaatgc acttgttgct gtaaagggaa     1020
cccctcttga ggatcagaag cctgttgaaa tatgggagat gattcgcatg atagcaactg     1080
```

-continued

```
cacgtatcgt aatgccaaaa gcaatggtca ggttatcagc tggcagagtt cgattctcca    1140
tgcctgagca ggcattgtgc tttcttgctg gtgcaaattc tatattcact ggtgaaaagc    1200
ttctcactac tcctaacaat gattttgatg ctgatcaact catgtttaaa gttcttggac    1260
ttctcccaaa agctccaagc ttacatgaag gtgaaactag tgtgacagaa gattataagg    1320
aagcagcttc ttctagttga                                                1340
```

<210> SEQ ID NO 12
<211> LENGTH: 374
<212> TYPE: PRT
<213> ORGANISM: Glycine max

<400> SEQUENCE: 12

```
Met Phe Leu Ala Arg Pro Ile Phe Arg Ala Pro Ser Leu Trp Ala Leu
1               5                   10                  15

His Ser Ser Tyr Ala Tyr Ser Ala Ser Ala Ala Ile Gln Ala
            20                  25                  30

Glu Arg Ala Ile Lys Glu Gly Pro Arg Asn Asp Trp Ser Arg Asp Gln
        35                  40                  45

Val Lys Ser Ile Tyr Asp Ser Pro Ile Leu Asp Leu Leu Phe His Gly
    50                  55                  60

Ala Gln Val His Arg His Ala His Asn Phe Arg Glu Val Gln Gln Cys
65                  70                  75                  80

Thr Leu Leu Ser Ile Lys Thr Gly Gly Cys Ser Glu Asp Cys Ser Tyr
                85                  90                  95

Cys Pro Gln Ser Ser Lys Tyr Asp Thr Gly Val Lys Arg Pro Ser Leu
            100                 105                 110

Met Asn Lys Glu Ala Val Leu Gln Ala Ala Lys Lys Ala Lys Glu Ala
        115                 120                 125

Gly Ser Thr Arg Phe Cys Met Gly Ala Ala Trp Arg Asp Thr Leu Gly
    130                 135                 140

Arg Lys Thr Asn Phe Asn Gln Ile Leu Glu Tyr Val Lys Asp Ile Arg
145                 150                 155                 160

Asp Met Gly Met Glu Val Cys Cys Thr Leu Gly Met Leu Glu Lys Gln
                165                 170                 175

Gln Ala Val Glu Leu Lys Lys Ala Gly Leu Thr Ala Tyr Asn His Asn
            180                 185                 190

Leu Asp Thr Ser Arg Glu Tyr Tyr Pro Asn Ile Ile Thr Thr Arg Thr
        195                 200                 205

Tyr Asp Glu Arg Leu Gln Thr Leu Glu Phe Val Arg Asp Ala Gly Ile
    210                 215                 220

Asn Val Cys Ser Gly Gly Ile Ile Gly Leu Gly Glu Ala Glu Glu Asp
225                 230                 235                 240

Arg Val Gly Leu Leu His Thr Leu Ser Thr Leu Pro Thr His Pro Glu
                245                 250                 255

Ser Val Pro Ile Asn Ala Leu Val Ala Val Lys Gly Thr Pro Leu Glu
            260                 265                 270

Asp Gln Lys Pro Val Glu Ile Trp Glu Met Ile Arg Met Ile Ala Thr
        275                 280                 285

Ala Arg Ile Val Met Pro Lys Ala Met Val Arg Leu Ser Ala Gly Arg
    290                 295                 300

Val Arg Phe Ser Met Pro Glu Gln Ala Leu Cys Phe Leu Ala Gly Ala
305                 310                 315                 320

Asn Ser Ile Phe Thr Gly Glu Lys Leu Leu Thr Thr Pro Asn Asn Asp
                325                 330                 335
```

Phe Asp Ala Asp Gln Leu Met Phe Lys Val Leu Gly Leu Leu Pro Lys
            340                 345                 350

Ala Pro Ser Leu His Glu Gly Glu Thr Ser Val Thr Glu Asp Tyr Lys
        355                 360                 365

Glu Ala Ala Ser Ser Ser
    370

<210> SEQ ID NO 13
<211> LENGTH: 479
<212> TYPE: DNA
<213> ORGANISM: Glycine max

<400> SEQUENCE: 13
ggcgactctc agaacttccc tatcacgatc cctcatcctc cttcgctcca ataccctaa      60 actcgcacct atctcttcct ctgttcgtct tcaagttcaa aagtcgagaa actatggtac    120
cgtatcatct gttcctcctc aagctacaga acatcaagc acatcaccta gtaaggatgt     180
ctaccaagaa gcactcaacg caactgaacc ccgcagcaat tggacaagag aagaaatcaa    240
ggcgatctat gataagccat tgatggagtt atgttgggt gctggtagtt tgcacaggaa     300
attccatata cctggggcta ttcagatgtg tacattgttg aacatcaaga cgggtggttg    360
ctcggaggga ttgttcttac tggcgcccaa tcatcccgct accaaaccgg tctcaaagcc   420
ctccaaaaat ggtcctccgt cgaatctgtc ctcgcaagcc gccccgcatc gccaaaaga    479

<210> SEQ ID NO 14
<211> LENGTH: 52
<212> TYPE: PRT
<213> ORGANISM: Glycine max

<400> SEQUENCE: 14

Arg Ser Asn Trp Thr Arg Glu Glu Ile Lys Ala Ile Tyr Asp Lys Pro
1               5                   10                  15

Leu Met Glu Leu Cys Trp Gly Ala Gly Ser Leu His Arg Lys Phe His
            20                  25                  30

Ile Pro Gly Ala Ile Gln Met Cys Thr Leu Leu Asn Ile Lys Thr Gly
        35                  40                  45

Gly Cys Ser Glu
    50

<210> SEQ ID NO 15
<211> LENGTH: 589
<212> TYPE: DNA
<213> ORGANISM: Triticum aestivum
<220> FEATURE:
<221> NAME/KEY: Unsure
<222> LOCATION: (321)..(321)
<223> OTHER INFORMATION: n = A, C, G, or T
<221> NAME/KEY: Unsure
<222> LOCATION: (332)..(332)
<223> OTHER INFORMATION: n = A, C, G, or T
<221> NAME/KEY: Unsure
<222> LOCATION: (335)..(336)
<223> OTHER INFORMATION: n = A, C, G, or T
<221> NAME/KEY: Unsure
<222> LOCATION: (403)..(403)
<223> OTHER INFORMATION: n = A, C, G, or T
<221> NAME/KEY: Unsure
<222> LOCATION: (407)..(407)
<223> OTHER INFORMATION: n = A, C, G, or T
<221> NAME/KEY: Unsure
<222> LOCATION: (516)..(516)
<223> OTHER INFORMATION: n = A, C, G, or T
<221> NAME/KEY: Unsure
<222> LOCATION: (539)..(539)

```
<223> OTHER INFORMATION: n = A, C, G, or T
<221> NAME/KEY: Unsure
<222> LOCATION: (547)..(547)
<223> OTHER INFORMATION: n = A, C, G, or T
<221> NAME/KEY: Unsure
<222> LOCATION: (550)..(550)
<223> OTHER INFORMATION: n = A, C, G, or T
<221> NAME/KEY: Unsure
<222> LOCATION: (555)..(555)
<223> OTHER INFORMATION: n = A, C, G, or T
<221> NAME/KEY: Unsure
<222> LOCATION: (577)..(578)
<223> OTHER INFORMATION: n = A, C, G, or T

<400> SEQUENCE: 15
agatgccgtc ctagaagcag caaaaaaggc aaaggaggct gggagcaccc gattttgcat     60
gggagccgca tggagagaga caattggcag gaaaacaaat ttcaaccaga ttcttgaata    120
tgtcaaggac ataagaggta tgggcatgga ggtctgttgc accctgggca tgctagagaa    180
acaacaagct gaagaactcc aagaaggctg gactttacag cttataatca taacctaaga    240
tacatccaag agaatattac ccccaacatt tattcctaca agattccgtt accgatggat    300
tagatttacc agctcctttc nagcatgtcc cnttnnaagc tgggaattaa gccgtcctgg    360
tcccaaggtg ggaatttatt gggcccttg ggagaaggcc ggnaggnaaa cccgtttttt     420
aggctggttt gccatacact gggccacttt tttgcccaac acaccccaag agagcgttcc    480
cctatccaat gcatttgatt gccctgtcca agggancctc ccttccaagg ttttaaaanc    540
cctgttnaan atatnggaaa ttattnccgc atgattnncc aacccacgg                589

<210> SEQ ID NO 16
<211> LENGTH: 78
<212> TYPE: PRT
<213> ORGANISM: Triticum aestivum
<220> FEATURE:
<221> NAME/KEY: UNSURE
<222> LOCATION: (69)..(69)
<223> OTHER INFORMATION: Xaa = any amino acid

<400> SEQUENCE: 16

Asp Ala Val Leu Glu Ala Ala Lys Lys Ala Lys Glu Ala Gly Ser Thr
1               5                   10                  15

Arg Phe Cys Met Gly Ala Ala Trp Arg Glu Thr Ile Gly Arg Lys Thr
            20                  25                  30

Asn Phe Asn Gln Ile Leu Glu Tyr Val Lys Asp Ile Arg Gly Met Gly
        35                  40                  45

Met Glu Val Cys Cys Thr Leu Gly Met Leu Glu Lys Gln Gln Ala Glu
    50                  55                  60

Glu Leu Gln Glu Xaa Asp Phe Thr Ala Tyr Asn His Asn Leu
65                  70                  75

<210> SEQ ID NO 17
<211> LENGTH: 1396
<212> TYPE: DNA
<213> ORGANISM: Hordeum vulgare

<400> SEQUENCE: 17
gcaccacaac tccctcggca gtatcgccta gtgcagcagc ggctccgttc cggccagctt     60
tgctcgccga gccggccatg atgctgctgc tcgcgcgcag ccttcgctcc cgcgtccggt    120 ccccttcgc ctccgccgtt agcgccgcgc ccttctcatc ggtatcggcg gccgcggcgg    180
aggcggagcg ggcggtgcgg gacgggccca ggaacgactg gacccgcccc gagatccagg    240
ccatctacga ctccccgctc ctcgacctcc tcttccacgg ggctcaagtc cataggaatg    300
```

```
tccataaatt tagagaagtg caacaatgca cacttctttc aataaagact ggtgggtgca    360
gcgaagattg ttcatactgc ccacagtctt caagatacag taccggattg aaggctgaaa    420
aattaatgaa gaaagatgcc gtcctagaag cagctaaaaa ggcaaaggag ctgggagca     480 cccgattttg catgggagcc gcatggagag agacaattgg caggaaaaca aacttcaacc    540
agattcttga atatgtcaag gacataagag gtatgggcat ggaggtctgt tgcaccctgg    600
gcatgctaga gaaacagcaa gctgaagaac tcaagaaggc tggacttaca gcttataatc    660
ataacctaga tacatcaaga gaatattacc cgaacattat ttctacaaga tcgtatgatg    720
atagattaca gactcttcag catgtccgtg aagctggaat aagcgtctgc tcaggtggaa    780
ttattggtct tggagaggcg gaggaagacc gtgtagggct gttgcataca ctggccactt    840
tgccaacaca cccagagagt gttcctatca atgcattgat tgctgtcaaa ggcacgcctc    900
ttcaggatca gaagcctgta gagatatggg aaatgatccg catgattgcc agcgctcgga    960
ttgtgatgcc aaaggcaatg gtgagacttt cggcagggcg agtacggttc tccatgccag    1020
agcaagctct ctgctttctt gctggggcca actcgatctt cgccggtgaa aagctcctga    1080
caactgcaaa caacgacttt gatgcggacc aggcaatgtt caagatcctt ggcctgattc    1140
ccaaggcacc gaactttggc gatgaggagg ccaccgtggc atcatccacg gagagatgtg    1200
agcaagccgc ttcgatgtaa aatgttggta tagattctcg agaccacatc cggtgcaaaa    1260
ctggcaccat tatctccagc tagagctttg tactgtaggg atcatgatat tttgtactcc    1320
ctccgttcct aaatataagt cttttaagcg atttcaaaaa aaaaaaaaaa aaaaaaaaaa    1380
aaaaaaaaaa aaaaaa                                                     1396
```

<210> SEQ ID NO 18
<211> LENGTH: 405
<212> TYPE: PRT
<213> ORGANISM: Hordeum vulgare

<400> SEQUENCE: 18

```
Thr Thr Thr Pro Ser Ala Val Ser Pro Ser Ala Ala Ala Pro Phe
 1               5                  10                  15

Arg Pro Ala Leu Leu Ala Glu Pro Ala Met Met Leu Leu Ala Arg
                20                  25                  30

Ser Leu Arg Ser Arg Val Arg Ser Pro Phe Ala Ser Ala Val Ser Ala
            35                  40                  45

Ala Pro Phe Ser Ser Val Ser Ala Ala Ala Glu Ala Glu Arg Ala
        50                  55                  60

Val Arg Asp Gly Pro Arg Asn Asp Trp Thr Arg Pro Glu Ile Gln Ala
65                  70                  75                  80

Ile Tyr Asp Ser Pro Leu Leu Asp Leu Leu Phe His Gly Ala Gln Val
                85                  90                  95

His Arg Asn Val His Lys Phe Arg Glu Val Gln Gln Cys Thr Leu Leu
                100                 105                 110

Ser Ile Lys Thr Gly Gly Cys Ser Glu Asp Cys Ser Tyr Cys Pro Gln
            115                 120                 125

Ser Ser Arg Tyr Ser Thr Gly Leu Lys Ala Glu Lys Leu Met Lys Lys
        130                 135                 140

Asp Ala Val Leu Glu Ala Ala Lys Lys Ala Lys Glu Ala Gly Ser Thr
145                 150                 155                 160

Arg Phe Cys Met Gly Ala Ala Trp Arg Glu Thr Ile Gly Arg Lys Thr
                165                 170                 175
```

```
Asn Phe Asn Gln Ile Leu Glu Tyr Val Lys Asp Ile Arg Gly Met Gly
            180                 185                 190
Met Glu Val Cys Cys Thr Leu Gly Met Leu Glu Lys Gln Gln Ala Glu
        195                 200                 205
Glu Leu Lys Lys Ala Gly Leu Thr Ala Tyr Asn His Asn Leu Asp Thr
    210                 215                 220
Ser Arg Glu Tyr Tyr Pro Asn Ile Ile Ser Thr Arg Ser Tyr Asp Asp
225                 230                 235                 240
Arg Leu Gln Thr Leu Gln His Val Arg Glu Ala Gly Ile Ser Val Cys
                245                 250                 255
Ser Gly Gly Ile Ile Gly Leu Gly Glu Ala Glu Asp Arg Val Gly
            260                 265                 270
Leu Leu His Thr Leu Ala Thr Leu Pro Thr His Pro Glu Ser Val Pro
        275                 280                 285
Ile Asn Ala Leu Ile Ala Val Lys Gly Thr Pro Leu Gln Asp Gln Lys
    290                 295                 300
Pro Val Glu Ile Trp Glu Met Ile Arg Met Ile Ala Ser Ala Arg Ile
305                 310                 315                 320
Val Met Pro Lys Ala Met Val Arg Leu Ser Ala Gly Arg Val Arg Phe
                325                 330                 335
Ser Met Pro Glu Gln Ala Leu Cys Phe Leu Ala Gly Ala Asn Ser Ile
            340                 345                 350
Phe Ala Gly Glu Lys Leu Leu Thr Thr Ala Asn Asn Asp Phe Asp Ala
        355                 360                 365
Asp Gln Ala Met Phe Lys Ile Leu Gly Leu Ile Pro Lys Ala Pro Asn
    370                 375                 380
Phe Gly Asp Glu Glu Ala Thr Val Ala Ser Ser Thr Glu Arg Cys Glu
385                 390                 395                 400
Gln Ala Ala Ser Met
                405

<210> SEQ ID NO 19
<211> LENGTH: 1467
<212> TYPE: DNA
<213> ORGANISM: Zea mays

<400> SEQUENCE: 19
gcacgagtcc aatcgggtgg cagtttttaa ggaaaccagg gaccgcagca gcaagccgcc      60
ccagccgacg aggcgaggag cgtgcaattc cgtagctgca acgaactccc tcgaccgtat     120
cgcccgctgc tcctctatcc ctttcctgct gctgctacta ccttaagcta tcactatcat     180
ggccttgatg ctgctagcgc gcaacctgcg ctcccgcctc cgcccaccgc tcgccgccgc     240
cgcggcgttc tcgtcggccg cggcggaggc ggagagggcg atacgggacg ggccgcggaa     300
cgactggagc cggcccgaga tccaggccgt ctacgactca ccgctcctcg acctcctctt     360
tcacggggct cagtcatcaa gatacaacac tggattgaag gcccaaaaat tgatgaacaa     420
atatgctgtc ttggaagcag caaaaaaggc aaaagagtct gggagcaccc gttttttgcat     480 gggagctgca tggagagaaa ccattggcag gaaatcaaac ttcaaccaga ttcttgaata     540
tgtcaaggaa ataaggggta tgggcatgga ggtctgttgc acactaggca tgatagagaa     600
acaacaagct gaagaactca agaaggctgg acttacagca tataatcata acctagatac     660
atcaagagag tattatccca acattattac cacaagatca tatgatgata gactgcagac     720
tcttgagcat gtccgtgaag ctggaataag catctgctca ggtggaatca ttggtcttgg     780
tgaagcagag gaggaccggg tagggttgtt gcatacccta gctaccttgc ctacacaccc     840
```

```
agagagcgtt cctattaatg cattggttgc tgtaaaaggc acacctcttg aggaccagaa    900
gcctgtagag atctgggaaa tgatccgcat gatcgccact gctcggatca cgatgccaaa    960
ggcaatggtg aggcttcag caggccgagt acgttctcg atgccagaac aagcgctgtg     1020
cttcctcgct ggggccaact ccatctttgc cggcgagaaa cttctcacaa ccgcaaacaa    1080
cgactttgat gcggaccagg cgatgttcaa gatccttggc ctgatcccca aggctccaag    1140
ctttggcgag gaagaggcgt ctgcggcggc tcccacagaa tccgagaggt ctgagcaagc    1200
tgcttcgatg tagaatatat acatatcatt accgattatc cgtatcacgg ttggggcgaa    1260
actagaacta ccgttgtagc tagagcattg gattgtagaa accacaacat ttcattattt    1320
tgtaattgct tgagactgaa tgggggatac ccatgtcggg ctagatcaat ggacaacttc    1380
cacacaacca aatccaaaca ttgaaactca tttttcatca cagttttaat aaacttctcc    1440
cacttatctt aaaaaaaaaa aaaaaaa                                        1467
```

<210> SEQ ID NO 20
<211> LENGTH: 344
<212> TYPE: PRT
<213> ORGANISM: Zea mays

<400> SEQUENCE: 20

```
Met Ala Leu Met Leu Leu Ala Arg Asn Leu Arg Ser Arg Leu Arg Pro
1               5                   10                  15

Pro Leu Ala Ala Ala Ala Phe Ser Ser Ala Ala Glu Ala Glu
            20                  25                  30

Arg Ala Ile Arg Asp Gly Pro Arg Asn Asp Trp Ser Arg Pro Glu Ile
        35                  40                  45

Gln Ala Val Tyr Asp Ser Pro Leu Leu Asp Leu Leu Phe His Gly Ala
    50                  55                  60

Gln Ser Ser Arg Tyr Asn Thr Gly Leu Lys Ala Gln Lys Leu Met Asn
65                  70                  75                  80

Lys Tyr Ala Val Leu Glu Ala Lys Lys Ala Lys Glu Ser Gly Ser
                85                  90                  95

Thr Arg Phe Cys Met Gly Ala Ala Trp Arg Glu Thr Ile Gly Arg Lys
            100                 105                 110

Ser Asn Phe Asn Gln Ile Leu Glu Tyr Val Lys Glu Ile Arg Gly Met
        115                 120                 125

Gly Met Glu Val Cys Cys Thr Leu Gly Met Ile Glu Lys Gln Gln Ala
    130                 135                 140

Glu Glu Leu Lys Lys Ala Gly Leu Thr Ala Tyr Asn His Asn Leu Asp
145                 150                 155                 160

Thr Ser Arg Glu Tyr Tyr Pro Asn Ile Ile Thr Thr Arg Ser Tyr Asp
                165                 170                 175

Asp Arg Leu Gln Thr Leu Glu His Val Arg Glu Ala Gly Ile Ser Ile
            180                 185                 190

Cys Ser Gly Gly Ile Ile Gly Leu Gly Glu Ala Glu Asp Arg Val
        195                 200                 205

Gly Leu Leu His Thr Leu Ala Thr Leu Pro Thr His Pro Glu Ser Val
    210                 215                 220

Pro Ile Asn Ala Leu Val Ala Val Lys Gly Thr Pro Leu Glu Asp Gln
225                 230                 235                 240

Lys Pro Val Glu Ile Trp Glu Met Ile Arg Met Ile Ala Thr Ala Arg
                245                 250                 255

Ile Thr Met Pro Lys Ala Met Val Arg Leu Ser Ala Gly Arg Val Arg
```

```
                260                265                 270
Phe Ser Met Pro Glu Gln Ala Leu Cys Phe Leu Ala Gly Ala Asn Ser
            275                 280                 285

Ile Phe Ala Gly Glu Lys Leu Leu Thr Thr Ala Asn Asn Asp Phe Asp
    290                 295                 300

Ala Asp Gln Ala Met Phe Lys Ile Leu Gly Leu Ile Pro Lys Ala Pro
305                 310                 315                 320

Ser Phe Gly Glu Glu Glu Ala Ser Ala Ala Ala Pro Thr Glu Ser Glu
                325                 330                 335

Arg Ser Glu Gln Ala Ala Ser Met
            340

<210> SEQ ID NO 21
<211> LENGTH: 1515
<212> TYPE: DNA
<213> ORGANISM: Zea mays

<400> SEQUENCE: 21
ggccccagcc gacgaggcga ggagcgtgca attccgtagc tgcaactgca acgaactccc     60
tccctccctc gaccgtatcg cccgctgctc ctctatccct ttcctgctgc tgctactacc    120
ttaagctatc atggccttga tgctgctagc gcgcaacctg cgctcccgcc tccgcccacc    180
gctcgccgcc gccgcggcgt tctcgtcggc gcggcggag gcggagggg cgatacggga     240
cgggccgcgg aacgactgga gccggcccga gatccaggcc gtctacgact accgctcct     300
cgacctcctc tttcacgggg ctcaggtcca gagaaatgtc cataaattca gagaagtgca    360
gcaatgcaca cttctttcaa tcaagactgg tggatgcagt gaagattgtt cttactgtcc    420
tcagtcatca agatacaaca ctggattgaa ggcccaaaaa ttgatgaaca agatgctgt     480
cttggaagca gcaaaaaagg caaagagtc tgggagcacc cgttttgca tgggagctgc     540
atggagagaa accattggca ggaaatcaaa cttcaaccag attcttgaat atgtcaagga    600
ataaggggt atgggcatgg aggtctgttg cacactaggc atgatagaga acaacaagc     660
tgaagaactc aagaaggctg gacttacagc atataatcat aacctagata catcaagaga    720
gtattatccc aacattatta ccacaagatc atatgatgat agactgcaga ctcttgagca    780
tgtccgtgaa gctggaataa gcatctgctc aggtggaatc attggtcttg gtgaagcaga    840
ggaggaccgg gtagggttgt tgcatacccct agctaccttg cctacacacc cagagagcgt    900
tcctattaat gcattggttg ctgtaaaagg cacacctctt gaggaccaga gcctgtaga     960
gatctgggaa atgatccgca tgatcgccac tgctcggatc acgatgccaa aggcaatggt   1020
gaggctttca gcaggccgag tacggttctc gatgccagaa caagcgctgt gcttcctcgc   1080
tggggccaac tccatctttg ccggcgagaa acttctcaca accgcaaaca acgactttga   1140
tgcggaccag gcgatgttca agatccttgg cctgatcccc aaggctccaa gctttggcga   1200
ggaagaggtg tctgcggcgg ctcccgcaga atccgagagg tctgagcaag ctgcttcgat   1260
gtagaatata tacatatcat taccgattat ccgtatcacg gttggggcga aactagaact   1320
accgttgtag ctagagcatt ggattgtaga accacaaca tttcattatt ttgtaattgc   1380
ttgagactga atgggggata cccatgtcgg gctagatcaa aaaaaaaaaa aaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaa                                                    1515

<210> SEQ ID NO 22
<211> LENGTH: 377
```

```
<212> TYPE: PRT
<213> ORGANISM: Zea mays

<400> SEQUENCE: 22

Met Ala Leu Met Leu Ala Arg Asn Leu Arg Ser Arg Leu Arg Pro
 1               5                  10                  15

Pro Leu Ala Ala Ala Ala Phe Ser Ser Ala Ala Ala Glu Ala Glu
            20                  25                  30

Arg Ala Ile Arg Asp Gly Pro Arg Asn Asp Trp Ser Arg Pro Glu Ile
        35                  40                  45

Gln Ala Val Tyr Asp Ser Pro Leu Leu Asp Leu Leu Phe His Gly Ala
    50                  55                  60

Gln Val His Arg Asn Val His Lys Phe Arg Glu Val Gln Gln Cys Thr
65                  70                  75                  80

Leu Leu Ser Ile Lys Thr Gly Gly Cys Ser Glu Asp Cys Ser Tyr Cys
                85                  90                  95

Pro Gln Ser Ser Arg Tyr Asn Thr Gly Leu Lys Ala Gln Lys Leu Met
            100                 105                 110

Asn Lys Asp Ala Val Leu Glu Ala Ala Lys Ala Lys Glu Ser Gly
        115                 120                 125

Ser Thr Arg Phe Cys Met Gly Ala Ala Trp Arg Glu Thr Ile Gly Arg
    130                 135                 140

Lys Ser Asn Phe Asn Gln Ile Leu Glu Tyr Val Lys Glu Ile Arg Gly
145                 150                 155                 160

Met Gly Met Glu Val Cys Cys Thr Leu Gly Met Ile Glu Lys Gln Gln
                165                 170                 175

Ala Glu Glu Leu Lys Lys Ala Gly Leu Thr Ala Tyr Asn His Asn Leu
            180                 185                 190

Asp Thr Ser Arg Glu Tyr Tyr Pro Asn Ile Ile Thr Thr Arg Ser Tyr
        195                 200                 205

Asp Asp Arg Leu Gln Thr Leu Glu His Val Arg Glu Ala Gly Ile Ser
    210                 215                 220

Ile Cys Ser Gly Gly Ile Ile Gly Leu Gly Glu Ala Glu Glu Asp Arg
225                 230                 235                 240

Val Gly Leu Leu His Thr Leu Ala Thr Leu Pro Thr His Pro Glu Ser
                245                 250                 255

Val Pro Ile Asn Ala Leu Val Ala Val Lys Gly Thr Pro Leu Glu Asp
            260                 265                 270

Gln Lys Pro Val Glu Ile Trp Glu Met Ile Arg Met Ile Ala Thr Ala
        275                 280                 285

Arg Ile Thr Met Pro Lys Ala Met Val Arg Leu Ser Ala Gly Arg Val
    290                 295                 300

Arg Phe Ser Met Pro Glu Gln Ala Leu Cys Phe Leu Ala Gly Ala Asn
305                 310                 315                 320

Ser Ile Phe Ala Gly Glu Lys Leu Leu Thr Thr Ala Asn Asn Asp Phe
                325                 330                 335

Asp Ala Asp Gln Ala Met Phe Lys Ile Leu Gly Leu Ile Pro Lys Ala
            340                 345                 350

Pro Ser Phe Gly Glu Glu Glu Val Ser Ala Ala Ala Pro Ala Glu Ser
        355                 360                 365

Glu Arg Ser Glu Gln Ala Ala Ser Met
    370                 375

<210> SEQ ID NO 23
<211> LENGTH: 1439
```

<212> TYPE: DNA
<213> ORGANISM: Zea mays

<400> SEQUENCE: 23

```
gcacgagggc gaggagcgtg caattccgta gctgcaacga actccctcga ccgtatcgcc      60
cgctgctcct ctatcccttt cctgctgctg ctactacctt aagctatcac tatcatggcc     120
ttgatgctgc tagcgcgcaa cctgcgctcc cgcctccgcc accgctcgc cgccgccgcg      180
gcgttctcgt cggccgcggc ggaggcggag agggcgatac gggacgggcc gcggaacgac     240
tggagccggc ccgagatcca ggccgtctac gactcaccgc tcctcgacct cctctttcac     300
ggggctcagg tccacagaaa tgtccataaa ttcagagaag tgcagcaatg cacacttctt     360
tcaatcaaga ctggtggatg cagtgaagat tgttcttact gtcctcagtc atcaagatac     420
aacactggat tgaaggccca aaaattgatg aacaaatatg ctgtcttgga agcagcaaaa     480
aaggcaaaag agtctgggag cacccgtttt tgcatgggag ctgcatggag agaaaccatt     540
ggcaggaaat caaacttcaa ccagattctt gaatatgtca aggaaataag gggtatgggc     600
atggaggtct gttgcacact aggcatgata gagaaacaac aagctgaaga actcaagaag     660
gctggactta cagcatataa tcataaccta gatacatcaa gagagtatta tcccaacatt     720
attaccacaa gatcatatga tgatagactg cagactcttg agcatgtccg tgaagctgga     780
ataagcatct gctcaggtgg aatcattggt cttggtgaag cagaggagga ccgggtaggg     840
ttgttgcata ccctagctac cttgcctaca cacccagaga gcgttcctat taatgcattg     900
gttgctgtaa aagcacacc tcttgaggac cagaagcctg tagagatctg ggaaatgatc     960
cgcatgatcg ccactgctcg gatcacgatg ccaaaggcaa tggtgaggct ttcagcaggc    1020
cgagtacggt tctcgatgcc agaacaagcg ctgtgcttcc tcgctgggc caactccatc    1080
tttgccggcg agaaacttct cacaaccgca acaacgact ttgatgcgga ccaggcgatg    1140
ttcaagatcc ttggcctgat ccccaaggct ccaagctttg gcgaggaaga ggcgtctgcg    1200
gcggctccca cagaatccga gaggtctgag caagctgctt cgatgtagaa tatatacata    1260
tcattaccga ttatccgtat cacggttggg gcgaaactag aactaccgtt gtagctagag    1320
cattggattg tagaaaccac aacatttcat tattttgtaa ttgcttgaga ctgaatgggg    1380
gatacccatg tcgggctaga tcaatggaca acttccacac aaaaaaaaaa aaaaaaaaa     1439
```

<210> SEQ ID NO 24
<211> LENGTH: 377
<212> TYPE: PRT
<213> ORGANISM: Zea mays

<400> SEQUENCE: 24

```
Met Ala Leu Met Leu Leu Ala Arg Asn Leu Arg Ser Arg Leu Arg Pro
 1               5                  10                  15

Pro Leu Ala Ala Ala Ala Ala Phe Ser Ser Ala Ala Glu Ala Glu
            20                  25                  30

Arg Ala Ile Arg Asp Gly Pro Arg Asn Asp Trp Ser Arg Pro Glu Ile
        35                  40                  45

Gln Ala Val Tyr Asp Ser Pro Leu Leu Asp Leu Leu Phe His Gly Ala
    50                  55                  60

Gln Val His Arg Asn Val His Lys Phe Arg Glu Val Gln Gln Cys Thr
65                  70                  75                  80

Leu Leu Ser Ile Lys Thr Gly Gly Cys Ser Glu Asp Cys Ser Tyr Cys
                85                  90                  95

Pro Gln Ser Ser Arg Tyr Asn Thr Gly Leu Lys Ala Gln Lys Leu Met
```

```
                100             105             110
Asn Lys Tyr Ala Val Leu Glu Ala Ala Lys Lys Ala Lys Glu Ser Gly
            115                 120                 125

Ser Thr Arg Phe Cys Met Gly Ala Ala Trp Arg Glu Thr Ile Gly Arg
    130                 135                 140

Lys Ser Asn Phe Asn Gln Ile Leu Glu Tyr Val Lys Glu Ile Arg Gly
145                 150                 155                 160

Met Gly Met Glu Val Cys Cys Thr Leu Gly Met Ile Glu Lys Gln Gln
                165                 170                 175

Ala Glu Glu Leu Lys Lys Ala Gly Leu Thr Ala Tyr Asn His Asn Leu
            180                 185                 190

Asp Thr Ser Arg Glu Tyr Tyr Pro Asn Ile Ile Thr Thr Arg Ser Tyr
        195                 200                 205

Asp Asp Arg Leu Gln Thr Leu Glu His Val Arg Glu Ala Gly Ile Ser
        210                 215                 220

Ile Cys Ser Gly Gly Ile Ile Gly Leu Gly Glu Ala Glu Glu Asp Arg
225                 230                 235                 240

Val Gly Leu Leu His Thr Leu Ala Thr Leu Pro Thr His Pro Glu Ser
                245                 250                 255

Val Pro Ile Asn Ala Leu Val Ala Val Lys Gly Thr Pro Leu Glu Asp
            260                 265                 270

Gln Lys Pro Val Glu Ile Trp Glu Met Ile Arg Met Ile Ala Thr Ala
        275                 280                 285

Arg Ile Thr Met Pro Lys Ala Met Val Arg Leu Ser Ala Gly Arg Val
    290                 295                 300

Arg Phe Ser Met Pro Glu Gln Ala Leu Cys Phe Leu Ala Gly Ala Asn
305                 310                 315                 320

Ser Ile Phe Ala Gly Glu Lys Leu Leu Thr Thr Ala Asn Asn Asp Phe
                325                 330                 335

Asp Ala Asp Gln Ala Met Phe Lys Ile Leu Gly Leu Ile Pro Lys Ala
            340                 345                 350

Pro Ser Phe Gly Glu Glu Glu Ala Ser Ala Ala Ala Pro Thr Glu Ser
        355                 360                 365

Glu Arg Ser Glu Gln Ala Ala Ser Met
    370                 375

<210> SEQ ID NO 25
<211> LENGTH: 1477
<212> TYPE: DNA
<213> ORGANISM: Argemone mexicana

<400> SEQUENCE: 25
gcacgagcat tcgagaaata aagagctgta aaattttag ggttttctg cataactcta       60 cactcgaagc ttcatcaata gaaatatcat aaacagaaga attcaaaatg cttaaagttc      120
aatctttgag agctcgtctt cgacctttga ttttcatttc tacattttct tctctctcat      180
catcttcttc ttcttcagct gctgctgttc aagcagaaag aacgattaaa gaaggtccaa      240
gaaacgattg gagcagagat gaaattaaat cggtttatga ttctccagtt ctcgatcttc      300
tcttccatgc agctcaagtc catagacatg ctcacaactt cagggaagtg cagcaatgta      360
ctcttctctc tgttaagaca ggtgggtgca gtgaagattg ttcatattgt ccacaatctt      420
ccaggtatga cactggagtg aaagcccaaa agctgatgaa caaggacgca gttctgcagg      480
cagcagaaaa ggcaaaggag gcgggtagta cacgttttctg catgggtgct gcatggagag      540
atacagtggg caggaagacc aacttcaaac agatcctcga atatgtaaaa gaaattcggg      600
```

-continued

```
gtatgggaat ggaggtatgc tgcactttag gcatgatcga gaagcagcaa gctgtggaac     660
tcaagcaggc tgggctcaca gcttacaatc ataatcttga tacttcaaga gagtattacc    720
ctaacatcat caccacaaga tcttacgatg agcgcttgga aactcttcag ttcgtccggg    780
aagcagggat caatgtctgc tcaggaggaa taatagggct aggagaagca gaggaggatc    840
gagttggtct tttgcataca ctagcaacgc ttccttcaca tccagaaagt gttcccatca    900
atgcattgct tgcagtcaaa ggcacacctc ttgaagatca gaagccagtt gaaatatggg    960
agatgattcg gatgattgct actgctagaa ttgtaatgcc aaaagcaatg gtcaggctat   1020
cagcaggtcg tgttcgattt tccatgtccg agcaagctct ctgcttcctt gctggcgcca   1080
attccatctt cactggtgag aaactattga caactcccaa caatgatttt gacgcagatc   1140
aaatgatgtt taagatttta gggctgacac caaaagctcc aaattttgac caaacatcaa   1200
catctttcga agccgagaga tgtgaacaag aagcaactgc gtcatagttc ttgcttcgat   1260
gagattatat atttatccaa atgaagaaat tcccgtccac cgtgtaagct tctttctttt   1320
acatgaagtt tctttgtatg aattatgaaa cctccaaaat aagctatact atttataaca   1380
ggaagttact gctaaatttt caattccatg ggaaatctat tttatgaact caaaaaaaaa   1440
aaaaaaaaaa aaaaaaaaaa aaaaaaaaaa aaaaaa                             1477
```

<210> SEQ ID NO 26
<211> LENGTH: 379
<212> TYPE: PRT
<213> ORGANISM: Argemone mexicana

<400> SEQUENCE: 26

```
Met Leu Lys Val Gln Ser Leu Arg Ala Arg Leu Arg Pro Leu Ile Phe
 1               5                  10                  15

Ile Ser Thr Phe Ser Ser Leu Ser Ser Ser Ser Ser Ser Ala Ala
                20                  25                  30

Ala Val Gln Ala Glu Arg Thr Ile Lys Glu Gly Pro Arg Asn Asp Trp
             35                  40                  45

Ser Arg Asp Glu Ile Lys Ser Val Tyr Asp Ser Pro Val Leu Asp Leu
         50                  55                  60

Leu Phe His Ala Ala Gln Val His Arg His Ala His Asn Phe Arg Glu
 65                  70                  75                  80

Val Gln Gln Cys Thr Leu Leu Ser Val Lys Thr Gly Gly Cys Ser Glu
                 85                  90                  95

Asp Cys Ser Tyr Cys Pro Gln Ser Ser Arg Tyr Asp Thr Gly Val Lys
            100                 105                 110

Ala Gln Lys Leu Met Asn Lys Asp Ala Val Leu Gln Ala Ala Glu Lys
        115                 120                 125

Ala Lys Glu Ala Gly Ser Thr Arg Phe Cys Met Gly Ala Ala Trp Arg
    130                 135                 140

Asp Thr Val Gly Arg Lys Thr Asn Phe Lys Gln Ile Leu Glu Tyr Val
145                 150                 155                 160

Lys Glu Ile Arg Gly Met Gly Met Glu Val Cys Cys Thr Leu Gly Met
                165                 170                 175

Ile Glu Lys Gln Gln Ala Val Glu Leu Lys Gln Ala Gly Leu Thr Ala
            180                 185                 190

Tyr Asn His Asn Leu Asp Thr Ser Arg Glu Tyr Tyr Pro Asn Ile Ile
        195                 200                 205

Thr Thr Arg Ser Tyr Asp Glu Arg Leu Glu Thr Leu Gln Phe Val Arg
    210                 215                 220
```

```
Glu Ala Gly Ile Asn Val Cys Ser Gly Gly Ile Ile Gly Leu Gly Glu
225                 230                 235                 240

Ala Glu Glu Asp Arg Val Gly Leu Leu His Thr Leu Ala Thr Leu Pro
            245                 250                 255

Ser His Pro Glu Ser Val Pro Ile Asn Ala Leu Leu Ala Val Lys Gly
        260                 265                 270

Thr Pro Leu Glu Asp Gln Lys Pro Val Glu Ile Trp Glu Met Ile Arg
    275                 280                 285

Met Ile Ala Thr Ala Arg Ile Val Met Pro Lys Ala Met Val Arg Leu
290                 295                 300

Ser Ala Gly Arg Val Arg Phe Ser Met Ser Glu Gln Ala Leu Cys Phe
305                 310                 315                 320

Leu Ala Gly Ala Asn Ser Ile Phe Thr Gly Leu Lys Leu Leu Thr Thr
                325                 330                 335

Pro Asn Asn Asp Phe Asp Ala Asp Gln Met Met Phe Lys Ile Leu Gly
            340                 345                 350

Leu Thr Pro Lys Ala Pro Asn Phe Asp Gln Thr Ser Thr Ser Phe Glu
        355                 360                 365

Ala Glu Arg Cys Glu Gln Glu Ala Thr Ala Ser
    370                 375

<210> SEQ ID NO 27
<211> LENGTH: 1526
<212> TYPE: DNA
<213> ORGANISM: Glycine max

<400> SEQUENCE: 27
gcacgagcta gtactgctcc ctctgcgact tcgtttcgta gagggatttt ggccgccaaa      60
taaacagtct caccataaac tccaaagtcc aacgctaaa  cgaaaccaaa ccccaaacac     120
aaataccgtt gttgtctgtt gtctctgtcg tgtctatatt cgcagatctc tcactcattc     180
tctgttgttt ctctgcccaa cttcgaattc gaaagcaaaa acatgttttt ggcgagaccc     240
attttccgag cacccctccct tgggcgttg  cactcttcct acgcgtattc ctctgcctca     300
gcagctgcaa ttcaagctga gagagccatc aaagaaggac ccagaaacga ttggagccga     360
gaccaagtca aatccatcta cgactctccc attctcgatc ttctcttcca tggggctcaa     420
gttcacagac atgctcataa cttcagggaa gttcagcagt gtactcttct gtctatcaaa     480
acaggagggt gcagtgaaga ttgttcctat tgtcctcaat cctctaagta tgatacagga     540
gtcaaaggcc aacgccttat gaacaaggaa gctgttctac aggctgcaaa gaaggcaaaa     600
gaggctggga gcactcgctt tgtatgggt  gctgcatgga gggatacact gggaagaaag     660
accaacttca accagatcct tgaatatgtg aaagacataa gggacatggg aatggaggtt     720
tgttgcaccc ttggcatgct ggagaaacag caggctgttg aactcaagaa ggcaggtctc     780
actgcctata atcacaatct tgacacttca agggagtatt atccaaacat catcacaaca     840
aggacttatg atgagcgtct tcaaacccctt gagtttgttc gtgatgcagg atcaatgtt      900 tgttctggag gaattatagg gcttggagaa gcagaggagg atcgtgtagg tttgttacat     960
acattgtcaa cacttcccac ccatccagag agtgttccta ttaatgcact tgttgctgta    1020
aagggaaccc ctcttgagga tcagaagcct gttgaaatat gggagatgat tcgcatgata    1080
gcaactgcac gtatcgtaat gccaaaagca atggtcaggt tatcagctgg cagagttcga    1140
ttctccatgc ctgagcaggc attgtgcttt cttgctggtg caaattctat attcactggt    1200
gaaaagcttc tcactactcc taacaatgat tttgatgctg atcaactcat gtttaaagtt    1260
```

```
cttggacttc tcccaaaagc tccaagctta catgaaggtg aaactagtgt gacagaagat   1320
tataaggaag cagcttcttc tagttgagtt gtcaacggtt tcaaaacaat atctgtgatc   1380
cttcaacttc tctaattgct cattagcatg tactgatgtt aggtttcatt gaatttgtct   1440
aatctcagct ttgaagacac aaactccaac acttaaaaat aaatattgaa attattgatt   1500
tttccctaaa aaaaaaaaaa aaaaaa                                       1526
```

<210> SEQ ID NO 28
<211> LENGTH: 415
<212> TYPE: PRT
<213> ORGANISM: Glycine max

<400> SEQUENCE: 28

```
Thr Lys Pro Asn Pro Lys His Lys Tyr Arg Cys Cys Leu Leu Ser Leu
 1               5                  10                  15

Ser Cys Leu Tyr Ser Gln Ile Ser His Ser Phe Ser Val Val Ser Leu
            20                  25                  30

Pro Asn Phe Glu Phe Glu Ser Lys Asn Met Phe Leu Ala Arg Pro Ile
        35                  40                  45

Phe Arg Ala Pro Ser Leu Trp Ala Leu His Ser Ser Tyr Ala Tyr Ser
    50                  55                  60

Ser Ala Ser Ala Ala Ile Gln Ala Glu Arg Ala Ile Lys Glu Gly
65                  70                  75                  80

Pro Arg Asn Asp Trp Ser Arg Asp Gln Val Lys Ser Ile Tyr Asp Ser
                85                  90                  95

Pro Ile Leu Asp Leu Leu Phe His Gly Ala Gln Val His Arg His Ala
            100                 105                 110

His Asn Phe Arg Glu Val Gln Gln Cys Thr Leu Leu Ser Ile Lys Thr
        115                 120                 125

Gly Gly Cys Ser Glu Asp Cys Ser Tyr Cys Pro Gln Ser Ser Lys Tyr
    130                 135                 140

Asp Thr Gly Val Lys Gly Gln Arg Leu Met Asn Lys Glu Ala Val Leu
145                 150                 155                 160

Gln Ala Ala Lys Lys Ala Lys Glu Ala Gly Ser Thr Arg Phe Cys Met
                165                 170                 175

Gly Ala Ala Trp Arg Asp Thr Leu Gly Arg Lys Thr Asn Phe Asn Gln
            180                 185                 190

Ile Leu Glu Tyr Val Lys Asp Ile Arg Asp Met Gly Met Glu Val Cys
        195                 200                 205

Cys Thr Leu Gly Met Leu Glu Lys Gln Gln Ala Val Glu Leu Lys Lys
    210                 215                 220

Ala Gly Leu Thr Ala Tyr Asn His Asn Leu Asp Thr Ser Arg Glu Tyr
225                 230                 235                 240

Tyr Pro Asn Ile Ile Thr Thr Arg Thr Tyr Asp Glu Arg Leu Gln Thr
                245                 250                 255

Leu Glu Phe Val Arg Asp Ala Gly Ile Asn Val Cys Ser Gly Gly Ile
            260                 265                 270

Ile Gly Leu Gly Glu Ala Glu Glu Asp Arg Val Gly Leu Leu His Thr
        275                 280                 285

Leu Ser Thr Leu Pro Thr His Pro Glu Ser Val Pro Ile Asn Ala Leu
    290                 295                 300

Val Ala Val Lys Gly Thr Pro Leu Glu Asp Gln Lys Pro Val Glu Ile
305                 310                 315                 320

Trp Glu Met Ile Arg Met Ile Ala Thr Ala Arg Ile Val Met Pro Lys
```

```
                  325               330               335
Ala Met Val Arg Leu Ser Ala Gly Arg Val Arg Phe Ser Met Pro Glu
                340               345               350

Gln Ala Leu Cys Phe Leu Ala Gly Ala Asn Ser Ile Phe Thr Gly Glu
                355               360               365

Lys Leu Leu Thr Thr Pro Asn Asn Asp Phe Asp Ala Asp Gln Leu Met
        370               375               380

Phe Lys Val Leu Gly Leu Leu Pro Lys Ala Pro Ser Leu His Glu Gly
385               390               395               400

Glu Thr Ser Val Thr Glu Asp Tyr Lys Glu Ala Ala Ser Ser Ser
                405               410               415

<210> SEQ ID NO 29
<211> LENGTH: 1659
<212> TYPE: DNA
<213> ORGANISM: Glycine max

<400> SEQUENCE: 29
```

| | | | | | |
|---|---|---|---|---|---|
| aaagagtgta | tacagataga | tttccaaact | ccactcactc | accactatgg | cgactctcag | 60 |
| aacttcccta | tcacgatccc | tcatcctcct | tcgctccaat | accccaaac | tcgcacctat | 120 |
| ctcttcctct | gttcgtcttc | aagttcaaaa | gtcgagaaac | tatggtaccg | tatcatctgt | 180 |
| tcctcctcaa | gctacagaaa | catcaagcac | atcacctagt | aaggatgtct | accaagaagc | 240 |
| actcaacgca | actgaacccc | gcagcaattg | acaagagaa | gaaatcaagg | cgatctatga | 300 |
| taagccattg | atggagttat | gttggggtgc | tggtagtttg | cacaggaaat | tccatatacc | 360 |
| tggggctatt | cagatgtgta | cattgttgaa | catcaagacg | gtggttgct | cggaggattg | 420 |
| ttcttactgc | gcccaatcat | cccgctacca | accggtctc | aaagcctcca | aaatggtctc | 480 |
| cgtcgaatct | gtcctcgcag | ccgcccgcat | cgccaaagac | aacggtagta | cacgtttctg | 540 |
| catgggagcc | gcgtggcgcg | atatgcgtgg | acgaaaaacc | aatctcaaaa | atgtcaaaac | 600 |
| aatggttagc | gagattcgcg | gaatgggtat | ggaagtatgt | gtcacgcttg | gtatgattga | 660 |
| tgcagagcaa | gctcaggaac | tcaaagaagc | cggtctcacg | gcttataatc | ataatgtgga | 720 |
| tacgtcgagg | gatttctatc | ccaaggttat | cacgaccagg | acttatgatg | agagattgga | 780 |
| taccattaag | aatgtgagag | aggccggaat | caatgtttgt | acgggtggaa | tcctcggatt | 840 |
| aggagaaaat | aagtctgacc | atattggact | tttggagacg | gttgctacgt | tgccttcgca | 900 |
| tccggaatca | tttcctgtga | acatgttagt | ggctatcaaa | ggaacaccac | tggaaggaaa | 960 |
| caagaaggtg | gaatttgaga | atatgttgag | aatggttgcg | acggctagaa | tcgtcatgcc | 1020 |
| taaaaccatc | gtgcgtttgg | cagctggaag | aggagaattg | agcgaggaac | aacaggtctt | 1080 |
| atgtttcatg | gccggagcca | atgccgtttt | cacaggagaa | acaatgttaa | ccacaccagc | 1140 |
| cgttggatgg | ggtgtcgatt | ccgtcgtttt | caacagatgg | ggattaagac | ccatggaaag | 1200 |
| tttcgaggtt | gaagccttga | gaacgataa | acctgccact | actaatacgg | aaataccggt | 1260 |
| agaggcaagt | aaggcagaga | tgccaggtac | agttgcttga | ttgattgttt | gatttggata | 1320 |
| cccagggcgt | ttggtgcgct | catcatctcg | agttttgca | aggagattcg | aacagtggaa | 1380 |
| gtgccgttgc | gccaccattg | ggattggcgt | atcggactga | gattgactgt | gccacgaaaa | 1440 |
| tgttttgcgc | tatcgtgtgt | tgtcatctcg | tgggaattta | gcgttgtttg | ttttgttttt | 1500 |
| ggttttgttt | gatgtgagag | aatgattgtt | tagaagggga | gaatgtatat | acggaacagt | 1560 |
| agaatatatt | cttgtctata | agattatata | ggataaaat | atataagctt | atcctcaaaa | 1620 |
| aaaaaaaaa | aaaaaaaaa | aaaaaaaaa | aaaaaaaa | | | 1659 |

```
<210> SEQ ID NO 30
<211> LENGTH: 417
<212> TYPE: PRT
<213> ORGANISM: Glycine max

<400> SEQUENCE: 30

Met Ala Thr Leu Arg Thr Ser Leu Ser Arg Ser Leu Ile Leu Leu Arg
1               5                   10                  15

Ser Asn Thr Pro Lys Leu Ala Pro Ile Ser Ser Val Arg Leu Gln
            20                  25                  30

Val Gln Lys Ser Arg Asn Tyr Gly Thr Val Ser Val Pro Pro Gln
        35                  40                  45

Ala Thr Glu Thr Ser Ser Thr Ser Pro Ser Lys Asp Val Tyr Gln Glu
50                      55                  60

Ala Leu Asn Ala Thr Glu Pro Arg Ser Asn Trp Thr Arg Glu Glu Ile
65                  70                  75                  80

Lys Ala Ile Tyr Asp Lys Pro Leu Met Glu Leu Cys Trp Gly Ala Gly
                85                  90                  95

Ser Leu His Arg Lys Phe His Ile Pro Gly Ala Ile Gln Met Cys Thr
            100                 105                 110

Leu Leu Asn Ile Lys Thr Gly Gly Cys Ser Glu Asp Cys Ser Tyr Cys
        115                 120                 125

Ala Gln Ser Ser Arg Tyr Gln Thr Gly Leu Lys Ala Ser Lys Met Val
130                 135                 140

Ser Val Glu Ser Val Leu Ala Ala Arg Ile Ala Lys Asp Asn Gly
145                 150                 155                 160

Ser Thr Arg Phe Cys Met Gly Ala Ala Trp Arg Asp Met Arg Gly Arg
                165                 170                 175

Lys Thr Asn Leu Lys Asn Val Lys Thr Met Val Ser Glu Ile Arg Gly
            180                 185                 190

Met Gly Met Glu Val Cys Val Thr Leu Gly Met Ile Asp Ala Glu Gln
        195                 200                 205

Ala Gln Glu Leu Lys Glu Ala Gly Leu Thr Ala Tyr Asn His Asn Val
210                 215                 220

Asp Thr Ser Arg Asp Phe Tyr Pro Lys Val Ile Thr Thr Arg Thr Tyr
225                 230                 235                 240

Asp Glu Arg Leu Asp Thr Ile Lys Asn Val Arg Glu Ala Gly Ile Asn
                245                 250                 255

Val Cys Thr Gly Gly Ile Leu Gly Leu Gly Glu Asn Lys Ser Asp His
            260                 265                 270

Ile Gly Leu Leu Glu Thr Val Ala Thr Leu Pro Ser His Pro Glu Ser
        275                 280                 285

Phe Pro Val Asn Met Leu Val Ala Ile Lys Gly Thr Pro Leu Glu Gly
290                 295                 300

Asn Lys Lys Val Glu Phe Glu Asn Met Leu Arg Met Val Ala Thr Ala
305                 310                 315                 320

Arg Ile Val Met Pro Lys Thr Ile Val Arg Leu Ala Ala Gly Arg Gly
                325                 330                 335

Glu Leu Ser Glu Glu Gln Gln Val Leu Cys Phe Met Ala Gly Ala Asn
            340                 345                 350

Ala Val Phe Thr Gly Glu Thr Met Leu Thr Thr Pro Ala Val Gly Trp
        355                 360                 365

Gly Val Asp Ser Val Val Phe Asn Arg Trp Gly Leu Arg Pro Met Glu
370                 375                 380
```

Ser Phe Glu Val Glu Ala Leu Lys Asn Asp Lys Pro Ala Thr Thr Asn
385                 390                 395                 400

Thr Glu Ile Pro Val Glu Ala Ser Lys Ala Glu Met Pro Gly Thr Val
            405                 410                 415

Ala

<210> SEQ ID NO 31
<211> LENGTH: 1032
<212> TYPE: DNA
<213> ORGANISM: Triticum aestivum

<400> SEQUENCE: 31

| | | | | | |
|---|---|---|---|---|---|
| gcacgagaga | tgccgtccta | gaagcagcaa | aaaaggcaaa | ggaggctggg | agcacccgat | 60 |
| tttgcatggg | agccgcatgg | agagagacaa | ttggcaggaa | aacaaatttc | aaccagattc | 120 |
| ttgaatatgt | caaggacata | agaggtatgg | gcatggaggt | ctgttgcacc | ctgggcatgc | 180 |
| tagagaaaca | acaagctgaa | gaactcaaga | aggctggact | tacagcttat | aatcataacc | 240 |
| tagatacatc | aagagaatat | accccaaca | ttatttctac | aagatcgtac | gatgatagat | 300 |
| tacagactct | tcagcatgtc | cgtgaagctg | gaataagcgt | ctgctcaggt | ggaattattg | 360 |
| gtcttggaga | ggcggaggaa | gaccgtgtag | ggctgttgca | tacactggcc | actttgccaa | 420 |
| cacacccaga | gagcgttcct | atcaatgcat | tgattgctgt | caaggcacg | cctcttcagg | 480 |
| atcagaagcc | tgtagagata | tgggaaatga | tccgcatgat | tgccagcgca | cggattgtga | 540 |
| tgccaaaggc | aatggtgaga | ctttcggcag | ggagagtacg | gttttccatg | ccagaacaag | 600 |
| ctctctgctt | tctcgctggg | gccaactcga | tcttcgccgg | tgaaaagctc | ctgacaactg | 660 |
| cgaacaatga | ctttgatgcg | gaccaggcaa | tgttcaagat | ccttggcctg | attcccaagg | 720 |
| ctccaaactt | tggcgatgaa | gaggtcatgg | tagcagcacc | cacggagaga | tgtgagcaag | 780 |
| ccgctttgat | gtaaaatgtc | ggtatagatt | ctcgagacca | catccggtgc | aaaactggca | 840 |
| ccattatctc | cacctagagt | tttgtactgt | agagatcatg | acattttata | gtaacttcag | 900 |
| attcatcgaa | ataaataggg | gggttctctg | caaaaaaaa | aaaaaaaaaa | aaaaaaaaaa | 960 |
| aaaaaaaaaa | aaaaaaaaaa | aaaaaaaaaa | aaaaaaaaa | aaaaaaaaa | aaaaaaaaaa | 1020 |
| aaaaaaaaaa | aa | | | | | 1032 |

<210> SEQ ID NO 32
<211> LENGTH: 263
<212> TYPE: PRT
<213> ORGANISM: Triticum aestivum

<400> SEQUENCE: 32

Thr Arg Asp Ala Val Leu Glu Ala Ala Lys Lys Ala Lys Glu Ala Gly
1               5                   10                  15

Ser Thr Arg Phe Cys Met Gly Ala Ala Trp Arg Glu Thr Ile Gly Arg
            20                  25                  30

Lys Thr Asn Phe Asn Gln Ile Leu Glu Tyr Val Lys Asp Ile Arg Gly
        35                  40                  45

Met Gly Met Glu Val Cys Cys Thr Leu Gly Met Leu Glu Lys Gln Gln
    50                  55                  60

Ala Glu Glu Leu Lys Lys Ala Gly Leu Thr Ala Tyr Asn His Asn Leu
65                  70                  75                  80

Asp Thr Ser Arg Glu Tyr Tyr Pro Asn Ile Ile Ser Thr Arg Ser Tyr
                85                  90                  95

Asp Asp Arg Leu Gln Thr Leu Gln His Val Arg Glu Ala Gly Ile Ser

```
                    100                 105                 110
Val Cys Ser Gly Gly Ile Ile Gly Leu Gly Glu Ala Glu Asp Arg
            115                 120                 125
Val Gly Leu Leu His Thr Leu Ala Thr Leu Pro Thr His Pro Glu Ser
        130                 135                 140
Val Pro Ile Asn Ala Leu Ile Ala Val Lys Gly Thr Pro Leu Gln Asp
145                 150                 155                 160
Gln Lys Pro Val Glu Ile Trp Glu Met Ile Arg Met Ile Ala Ser Ala
                165                 170                 175
Arg Ile Val Met Pro Lys Ala Met Val Arg Leu Ser Ala Gly Arg Val
            180                 185                 190
Arg Phe Ser Met Pro Glu Gln Ala Leu Cys Phe Leu Ala Gly Ala Asn
        195                 200                 205
Ser Ile Phe Ala Gly Glu Lys Leu Leu Thr Thr Ala Asn Asn Asp Phe
    210                 215                 220
Asp Ala Asp Gln Ala Met Phe Lys Ile Leu Gly Leu Ile Pro Lys Ala
225                 230                 235                 240
Pro Asn Phe Gly Asp Glu Glu Val Met Val Ala Ala Pro Thr Glu Arg
                245                 250                 255
Cys Glu Gln Ala Ala Leu Met
            260

<210> SEQ ID NO 33
<211> LENGTH: 378
<212> TYPE: PRT
<213> ORGANISM: Arabidopsis thaliana

<400> SEQUENCE: 33

Met Met Leu Val Arg Ser Val Phe Arg Ser Gln Leu Arg Pro Ser Val
1               5                   10                  15
Ser Gly Gly Leu Gln Ser Ala Ser Cys Tyr Ser Ser Leu Ser Ala Ala
            20                  25                  30
Ser Ala Glu Ala Glu Arg Thr Ile Arg Glu Gly Pro Arg Asn Asp Trp
        35                  40                  45
Ser Arg Asp Glu Ile Lys Ser Val Tyr Asp Ser Pro Leu Leu Asp Leu
    50                  55                  60
Leu Phe His Gly Ala Gln Val His Arg His Val His Asn Phe Arg Glu
65                  70                  75                  80
Val Gln Gln Cys Thr Leu Leu Ser Ile Lys Thr Gly Gly Cys Ser Glu
                85                  90                  95
Asp Cys Ser Tyr Cys Pro Gln Ser Ser Arg Tyr Ser Thr Gly Val Lys
            100                 105                 110
Ala Gln Arg Leu Met Ser Lys Asp Ala Val Ile Asp Ala Ala Lys Lys
        115                 120                 125
Ala Lys Glu Ala Gly Ser Thr Arg Phe Cys Met Gly Ala Ala Trp Arg
    130                 135                 140
Asp Thr Ile Gly Arg Lys Thr Asn Phe Ser Gln Ile Leu Glu Tyr Ile
145                 150                 155                 160
Lys Glu Ile Arg Gly Met Gly Met Glu Val Cys Cys Thr Leu Gly Met
                165                 170                 175
Ile Glu Lys Gln Gln Ala Leu Glu Leu Lys Lys Ala Gly Leu Thr Ala
            180                 185                 190
Tyr Asn His Asn Leu Asp Thr Ser Arg Glu Tyr Tyr Pro Asn Val Ile
        195                 200                 205
Thr Thr Arg Ser Tyr Asp Asp Arg Leu Glu Thr Leu Ser His Val Arg
```

```
            210                 215                 220
Asp Ala Gly Ile Asn Val Cys Ser Gly Gly Ile Ile Gly Leu Gly Glu
225                 230                 235                 240

Ala Glu Glu Asp Arg Ile Gly Leu Leu His Thr Leu Ala Thr Leu Pro
                245                 250                 255

Ser His Pro Glu Ser Val Pro Ile Asn Ala Leu Leu Ala Val Lys Gly
                260                 265                 270

Thr Pro Leu Glu Asp Gln Lys Pro Val Glu Ile Trp Glu Met Ile Arg
            275                 280                 285

Met Ile Gly Thr Ala Arg Ile Val Met Pro Lys Ala Met Val Arg Leu
        290                 295                 300

Ser Ala Gly Arg Val Arg Phe Ser Met Ser Glu Gln Ala Leu Cys Phe
305                 310                 315                 320

Leu Ala Gly Ala Asn Ser Ile Phe Thr Gly Glu Lys Leu Leu Thr Thr
                325                 330                 335

Pro Asn Asn Asp Phe Asp Ala Asp Gln Leu Met Phe Lys Thr Leu Gly
            340                 345                 350

Leu Ile Pro Lys Pro Pro Ser Phe Ser Glu Asp Asp Ser Glu Ser Glu
            355                 360                 365

Asn Cys Glu Lys Val Ala Ser Ala Ser His
370                 375

<210> SEQ ID NO 34
<211> LENGTH: 362
<212> TYPE: PRT
<213> ORGANISM: Saccharomyces cerevisiae

<400> SEQUENCE: 34

Met Phe Thr Arg Thr Ile Arg Gln Gln Ile Arg Arg Phe Phe Ala Leu
1               5                   10                  15

Phe Leu Val Arg Asn Asn Trp Thr Arg Glu Glu Ile Gln Lys Ile Tyr
                20                  25                  30

Asp Thr Pro Leu Ile Asp Leu Ile Phe Arg Ala Ala Ser Ile His Arg
            35                  40                  45

Lys Phe His Asp Pro Lys Lys Val Gln Gln Cys Thr Leu Leu Ser Ile
    50                  55                  60

Lys Thr Gly Gly Cys Thr Glu Asp Cys Lys Tyr Cys Ala Gln Ser Ser
65                  70                  75                  80

Arg Tyr Asn Thr Gly Val Lys Ala Thr Lys Leu Met Lys Ile Asp Glu
                85                  90                  95

Val Leu Glu Lys Ala Lys Ile Ala Lys Ala Lys Gly Ser Thr Arg Phe
            100                 105                 110

Cys Met Gly Ser Ala Trp Arg Asp Leu Asn Gly Arg Asn Arg Thr Phe
        115                 120                 125

Lys Asn Ile Leu Glu Ile Ile Lys Glu Val Arg Ser Met Asp Met Glu
    130                 135                 140

Val Cys Val Thr Leu Gly Met Leu Asn Glu Gln Gln Ala Lys Glu Leu
145                 150                 155                 160

Lys Asp Ala Gly Leu Thr Ala Tyr Asn His Asn Leu Asp Thr Ser Arg
                165                 170                 175

Glu Tyr Tyr Ser Lys Ile Ile Ser Thr Arg Thr Tyr Asp Glu Arg Leu
            180                 185                 190

Asn Thr Ile Asp Asn Leu Arg Lys Ala Gly Leu Lys Val Cys Ser Gly
        195                 200                 205

Gly Ile Leu Gly Leu Gly Glu Lys Lys His Asp Arg Val Gly Leu Ile
```

```
                210                 215                 220
His Ser Leu Ala Thr Met Pro Thr His Pro Glu Ser Val Pro Phe Asn
225                 230                 235                 240

Leu Leu Val Pro Ile Pro Gly Thr Pro Val Gly Asp Ala Val Lys Glu
                245                 250                 255

Arg Leu Pro Ile His Pro Phe Leu Arg Ser Ile Ala Thr Ala Arg Ile
                260                 265                 270

Cys Met Pro Lys Thr Ile Ile Arg Phe Ala Ala Gly Arg Asn Thr Cys
                275                 280                 285

Ser Glu Ser Glu Gln Ala Leu Ala Phe Met Ala Gly Ala Asn Ala Val
                290                 295                 300

Phe Thr Gly Glu Lys Met Leu Leu Leu Leu Phe Leu Asp Ser Asp
305                 310                 315                 320

Ser Gln Leu Phe Tyr Asn Trp Gly Leu Glu Gly Met Gln Ser Phe Glu
                325                 330                 335

Tyr Gly Thr Ser Thr Glu Gly Glu Asp Gly Thr Phe Thr Leu Pro Pro
                340                 345                 350

Lys Glu Arg Leu Ala Pro Ser Pro Ser Leu
                355                 360

<210> SEQ ID NO 35
<211> LENGTH: 363
<212> TYPE: PRT
<213> ORGANISM: Schizosaccharomyces pombe

<400> SEQUENCE: 35

Met Phe Thr Arg Thr Ile Arg Gln Gln Ile Arg Arg Ser Ser Ala Leu
1               5                   10                  15

Ser Leu Val Arg Asn Asn Trp Thr Arg Glu Glu Ile Gln Lys Ile Tyr
                20                  25                  30

Asp Thr Pro Leu Ile Asp Leu Ile Phe Arg Ala Ala Ser Ile His Arg
                35                  40                  45

Lys Phe His Asp Pro Lys Lys Val Gln Gln Cys Thr Leu Leu Ser Ile
            50                  55                  60

Lys Thr Gly Gly Cys Thr Glu Asp Cys Lys Tyr Cys Ala Gln Ser Ser
65                  70                  75                  80

Arg Tyr Asn Thr Gly Val Lys Ala Thr Lys Leu Met Lys Ile Asp Glu
                85                  90                  95

Val Leu Glu Lys Ala Lys Ile Ala Lys Ala Lys Gly Ser Thr Arg Phe
                100                 105                 110

Cys Met Gly Ser Ala Trp Arg Asp Leu Asn Gly Arg Asn Arg Thr Phe
                115                 120                 125

Lys Asn Ile Leu Glu Ile Ile Lys Glu Val Arg Ser Met Asp Met Glu
            130                 135                 140

Val Cys Val Thr Leu Gly Met Leu Asn Glu Gln Gln Ala Lys Glu Leu
145                 150                 155                 160

Lys Asp Ala Gly Leu Thr Ala Tyr Asn His Asn Leu Asp Thr Ser Arg
                165                 170                 175

Glu Tyr Tyr Ser Lys Ile Ile Ser Thr Arg Thr Tyr Asp Glu Arg Leu
                180                 185                 190

Asn Thr Ile Asp Asn Leu Arg Lys Ala Gly Leu Lys Val Cys Ser Gly
            195                 200                 205

Gly Ile Leu Gly Leu Gly Glu Lys His Asp Arg Val Gly Leu Ile
210                 215                 220

His Ser Leu Ala Thr Met Pro Thr His Pro Glu Ser Val Pro Phe Asn
```

-continued

```
              225                 230                 235                 240

Leu Leu Val Pro Ile Pro Gly Thr Pro Val Gly Asp Ala Val Lys Glu
                           245                 250                 255

Arg Leu Pro Ile His Pro Phe Leu Arg Ser Ile Ala Thr Ala Arg Ile
                           260                 265                 270

Cys Met Pro Lys Thr Ile Ile Arg Phe Ala Ala Gly Arg Asn Thr Cys
                   275                 280                 285

Ser Glu Ser Glu Gln Ala Leu Ala Phe Met Ala Gly Ala Asn Ala Val
               290                 295                 300

Phe Thr Gly Glu Lys Met Leu Thr Thr Pro Ala Val Ser Trp Asp Ser
       305                 310                 315                 320

Asp Ser Gln Leu Phe Tyr Asn Trp Gly Leu Glu Gly Met Gln Ser Phe
                           325                 330                 335

Glu Tyr Gly Thr Ser Thr Glu Gly Glu Asp Gly Thr Phe Thr Leu Pro
                           340                 345                 350

Pro Lys Glu Arg Leu Ala Pro Ser Pro Ser Leu
                           355                 360

<210> SEQ ID NO 36
<211> LENGTH: 12
<212> TYPE: PRT
<213> ORGANISM: biotin synthase conserved sequence element
<220> FEATURE:
<221> NAME/KEY: UNSURE
<222> LOCATION: (2)..(2)
<223> OTHER INFORMATION: Xaa represents any amino acid
<221> NAME/KEY: UNSURE
<222> LOCATION: (4)..(4)
<223> OTHER INFORMATION: Xaa represents any amino acid
<221> NAME/KEY: UNSURE
<222> LOCATION: (8)..(8)
<223> OTHER INFORMATION: Xaa represents any amino acid
<221> NAME/KEY: UNSURE
<222> LOCATION: (11)..(11)
<223> OTHER INFORMATION: Xaa represents any amino acid

<400> SEQUENCE: 36

Gly Xaa Cys Xaa Glu Asp Cys Xaa Tyr Cys Xaa Gln
1               5                   10
9
```